(12) United States Patent
Usuda et al.

(10) Patent No.: US 7,468,262 B2
(45) Date of Patent: Dec. 23, 2008

(54) **POLYNUCLEOTIDES ENCODING USEFUL POLYPEPTIDES IN *CORYNEBACTERIUM GLUTAMICUM SSP. LACTOFERMENTUM***

(75) Inventors: Yoshihiro Usuda, Kawasaki (JP);
Yousuke Nishio, Kawasaki (JP);
Kazuhiko Matsui, Kawasaki (JP);
Shinichi Sugimoto, Kawasaki (JP); Chie Koseki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 398 days.

(21) Appl. No.: 10/439,247

(22) Filed: May 16, 2003

(65) Prior Publication Data

US 2004/0229305 A1    Nov. 18, 2004

(51) Int. Cl.
*C12P 13/04* (2006.01)
*C12N 1/21* (2006.01)
*C12N 15/63* (2006.01)

(52) U.S. Cl. .................. 435/106; 435/183; 435/193; 435/252.3; 435/320.1; 536/23.1; 536/23.2

(58) Field of Classification Search ................ 536/23.1, 536/23.2; 435/320.1, 252.3
See application file for complete search history.

(56) References Cited

U.S. PATENT DOCUMENTS

2002/0197605 A1   12/2002   Nakagawa et al. ............. 435/6

FOREIGN PATENT DOCUMENTS

| WO | WO01/00802 | 1/2001 |
|---|---|---|
| WO | WO01/00804 | 1/2001 |
| WO | WO01/00805 | 1/2001 |
| WO | WO01/00842 | 1/2001 |
| WO | WO01/00843 | 1/2001 |
| WO | WO01/00844 | 1/2001 |
| WO | WO01/00845 | 1/2001 |
| WO | WO01/02583 | 1/2001 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

\* cited by examiner

*Primary Examiner*—Richard G Hutson
(74) *Attorney, Agent, or Firm*—Shelly Guest Cermak; Cermak, Kenealy & Vaidya LLP

(57) ABSTRACT

The present invention provides novel polypeptides and polynucleotides useful as biotechnological tools, specifically identified in a coryneform bacterium *Corynebacterium glutamicum* ssp. *lactofermentum* and methods of producing substances in organisms having enhanced or attenuated expression of these polypeptides and/or polynucleotides.

28 Claims, No Drawings

POLYNUCLEOTIDES ENCODING USEFUL POLYPEPTIDES IN *CORYNEBACTERIUM GLUTAMICUM SSP. LACTOFERMENTUM*

BACKGROUND OF THE INVENTION

1. Field of the Invention

The present invention relates to novel polynucleotides encoding proteins useful as biotechnological tools and for production of substances, specifically identified in a coryneform bacterium *Corynebacterium glutamicum* ssp. *lactofermentum* and fragments thereof, polypeptides encoded by the polynucleotides and fragments thereof, polynucleotide arrays comprising the polynucleotides and fragments thereof.

2. Discussion of the Background

In the field of biotechnology, there needs many tools, for example, DNA ligase, DNA polymerase, RNA polymerase, modification and restriction enzymes, and so on. In this field, variation of genes or enzymes is important for extension of applicable objects. Furthermore, modification and improvement of organisms are important for industrial production of useful substances, such as amino acids, nucleic acids, organic acids, sugars, and enzymes, (Faurie, R. and Thommel, J. Microbial Production of L-Amino Acids, Springer Verlag, 2002; Harris, T. J. R., Protein Production by Biotechnology (Elsevier Applied Biotechnology Series), Aspen Publishers, 1990). For aforementioned purpose, genetic engineering is one of the useful method and many genes have been known to be effective. Modification and restriction endonucleases, chaperone proteins, enzymes that caytalyze important reactions, and transporters of important substances are useful for organisms improvement of substance production.

For example, amino acids such as L-lysine, L-glutamic acid, L-threonine, L-leucine, L-isoleucine, L-valine and L-phenylalanine are industrially produced by fermentation by using microorganisms that belong to the genus *Corynebacterium*, *Brevibacterium*, *Bacillus*, *Escherichia*, *Streptomyces*, *Pseudomonas*, *Arthrobacter*, *Serratia*, *Penicillium*, *Candida* or the like. In order to improve the productivity of amino acids, strains of the aforementioned microorganisms that have been isolated from nature or artificial mutants thereof have been used. Various examples of modification of genes, such as amplification, deletion, and point mutation by using recombinant DNA techniques to increase the L-amino acid-producing ability have been disclosed (Faurie, R. and Thommel, J., Microbial Production of L-Amino Acids, Springer Verlag, 2002).

SUMMARY OF THE INVENTION

An object of the present invention is to provide novel tools or measures in the biotechnology filed. In addition to usage of genes itself, modification of genes, such as amplification, deletion, and point mutation by using recombinant DNA techniques provides an efficient method to improve the process of substance production.

Such a process includes organisms or cells, which express a protein comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO:18, SEQ ID NO:20, and SEQ ID NO:22.

In one embodiment the polypeptides are encoded by a polynucleotide selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:21. In another embodiment the polypeptides are encoded by other polynucleotides which have substantial identity to the herein described polynucleotides or those which hybridize under stringent conditions.

Another object of the invention is to provide polynucleotide sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:21; as well as those polynucleotides that have substantial identity to these nucleotide sequences, preferably at least 95% identity.

Another object of the invention is to provide isolated polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; as well as those polypeptides that have substantial identity to these amino acid sequences, preferably at least 95% identity.

A further object of the invention is a method for producing a protein or proteins by culturing host cells containing the herein described polynucleotides under conditions and for a time suitable for expression of the protein and collecting the protein produced thereby.

Another object is the use of host cells having the polynucleotides described herein to produce amino acids, as well as the use of such isolated polypeptides in the production of amino acids.

Other objects of the invention include methods of detecting nucleic acid sequences homologous to at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO: 19, and SEQ ID NO:21, particularly nucleic acid sequences encoding polypeptides that herein described proteins or polypeptides and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

*Corynebacterium glutamicum* ssp. *lactofermentum* is a coryneform bacterium having L-glutamic acid producing ability. The coryneform bacteria include the group of microorganisms defined in Bergey's Manual of Determinative Bacteriology, 8th edition, p. 599 (1974), which are aerobic Gram-positive rods having no acid resistance and no spore-forming ability aerobic and which can be used for the large-scale production of a variety of fine chemicals including amino acids, nucleic acids, and so on. *Corynebacterium glutamicum* ssp. *lactofermentum* has hitherto been classified into the genus *Brevibacterium* as *Brevibacterium lactofermentum*, but united into the genus *Corynebacterium* at present (Liebl, W. et. al., Int. J. Syst. Bacteriol., 41:255, 1991).

The polynucleotides of this invention can be used for tools for biotechnology and also can be used to improve microorganisms, which are used to produce useful substances, for example, by fermentative processes. Modulation of the expression of the polynucleotides encoding useful activities of the present invention can be used to modulate the production of one or more substances from an organism.

Restriction endonucleases are indispensable for recombinant DNA technology and the diversity of specificity for recognition sequences is important for their usefulness as a tool. Restriction-modification systems are classified into three main types, according to their subunit composition, cofactor requirements and some other features. All Restriction-modification systems comprise a pair of enzymatic activities—a DNA-methyltransferase and a restriction endonuclease, both recognizing the same short (4-8 bp) nucleotide sequence. Restriction endonucleases catalyze double-stranded cleavage of DNA, while the function of methylases is to protect genomic DNA from cleavage by cognate specific endonucleases (Bickele, T. and Kruger, D. H., Microbiol. Rev. 57:434-450, 1993). In recent days the usefulness of restriction-modification system for genome rearrangement has been reported (Handa, N., Nakayama, Y., Sadykov, M., and Kobayashi, I., Mol. Microbiol. 40:932-40, 2001; Kobayashi, I., Nucleic Acids Res. 29:3742-3756, 2001). The restriction-modification system is classified into three types, namely, type I, II, and III. The type I system consists of three subunits, HsdM (DNA methylase), HsdS (specificity protein), and HsdR (endonuclease) and function as complex of three subunits. The type III system contain two subunits, one of which, Mod can function alone as a modification methylase. The second subunit Res has no enzymatic activity when it is not complexed with Mod.

Molecular chaperones are substances that associate and stabilize proteins at intermediate stages of folding, assembly, movement across membranes, and degradation. It is widely recognized that co-expression molecular chaperones can assist recombinant protein folding expressed in *Escherichia coli* and that in at least some cases this leads to increased production of active proteins (Nishihara, K., Kanemori, M., Kitagawa, M., Yanagi, H., Yura, T. Appl. Environ. Microbiol, 64:1694-1699, 1998). The most abundant and physiologically important chaperones include DnaK, DnaJ, GrpE, GroEL, and GroES. The DnaK is a member of the highly conserved and ubiquitous stress-70 protein family, also known as the hsp70 family for heat shock protein-70, which bind to and stabilize unfolded conformations of short regions of peptide chains (Gross, C.A., 1996. Function and regulation of the heat shock proteins. pp. 1382-1399. In F. C. Neidhardt. R. Curtiss III, J. L. Ingraham. E. C. C. Lin, K. B. Low, B. Magasanik. W. S. Reznikoff, M. Riley, M. Schaechter and H. E. Umbarger (ed.), *Escherichia coil* and *Salmonella typhitmurium*: cellular and molecular biology $2^{nd}$ ed. vol. 1, American Society for Microbiology, Washington, D.C.).

Glutamate dehydrogenase (GDH) catalyses the conversion from 2-oxoglutarate and NAD(P)H to L-glutamate and NAD(P). L-Glutamate is an important metabolite, one of the primary ammonia assimilation products, a donor of amino groups in amino acid and purine biosynthesis, and a precursor of the L-glutamate family of amino acids. The *Corynebacterium glutamicum* gdh gene encoding NADP-dependent GDH has been isolated and analyzed (Bormann, E. R. et. al., Mol. Microbiol., 6:317-26, 1992), which is one of important enzyme for glutamate family amino acid production.

Proline and betaine (glycine-betaine) are major osmoprotectants in many organisms. The accumulation of osmoprotectants is an important process for the adaptation to damaging environmental conditions. The increase of osmoprotectants is achieved either by altering metabolism or by transport (Csonka, L. N., Microbiol. Rev. 53:121-147, 1989). The secondary transporter ProP mediates the uptake of compatible solutes and contribute to the osmotolerance (Peter, H. et. al. J. Bacteriol., 180:6005-12, 1998; Culham, D. E. et. al., Microbiology, 147:1657-70, 2001). In *Corynebacterium glutamicum*, four secondary carriers for compatible solutes have been identified, the high-affinity glycine betaine uptake system BetP (Peter, H. et. al. J. Biol. Chem. 273:2567-2574, 1998), the specific proline uptake system PutP (Peter, H. et. al., Arch. Microbiol. 168:143-51, 1997), the ectoine/proline/glycine uptake system EctP, and the proline/ectoine uptake system ProP (Peter, H. et. al., J. Bacteriol., 180:6005-12, 1998).

"Substantial identity" as used herein refers to polynucleotides and polypeptides which are at least 70%, preferably at least 80% and more preferably at least 90% to 95% identical to the polynucleotides and polypeptides, respectively, according to the present invention.

"Polynucleotide" as used herein relates to polyribonucleotides and polydeoxyribonucleotides, it being possible for these to be non-modified RNA or DNA or modified RNA or DNA.

"Polypeptides" as used herein are understood to mean peptides or proteins which comprise two or more amino acids bonded via peptide bonds. In particular, the term refers to polypeptides which are at least 70%, preferably at least 80% and more preferably at least 90% to 95% identical to the polypeptides according to the present invention. Included within the scope of the present invention are polypeptide fragments of the polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22 or those which are identical to those described herein.

"Polynucleotides which encode the polypeptide" of the invention as used herein is understood to mean the sequences exemplified in this application as well as those sequences which have substantial identity to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:21, and which encode a molecule having one or more of the bioactivities of the associated gene products. Preferably, such polynucleotides are those which are at least 70%, preferably at least 80% and more preferably at least 90% to 95% identical to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, and SEQ ID NO:21.

Polynucleotides according to the invention may be employed as probes to isolate and/or identify RNA, cDNA and DNA molecules, e.g., full-length genes or polynucleotides which code for the polypeptides described herein. Likewise, the probes can be employed to isolate nucleic acids, polynucleotides or genes which have a high sequence similarity or identity with the polynucleotides of the invention.

Polynucleotides of the invention may also be used to design primers useful for the polymerase chain reaction to amplify, identify and/or isolate full-length DNA, RNA or other polynucleotides with high sequence homology or identity to the polynucleotides of the invention, as well as, polynucleotides that encode the polypeptides of the invention. Preferably, probes or primers are at least 15, 16, 17, 18, 19, 20, 21, 22, 23, 24, 25, 26, 27, 28, 29 or 30 nucleotides in length. Oligonucleotides with a length of at least 35, 40, 45, 50, 100, 150, 200, 250 or 300 nucleotides may also be used.

Methods of DNA sequencing are described inter alia by Sanger et al. (Proc. Natl. Acad. Sci. USA, 74:5463-5467, 1977).

A person skilled in the art will find instructions for amplification of DNA sequences with the aid of the polymerase chain reaction (PCR) inter alia in the handbook by Gait: Oligonucleotide Synthesis: A Practical Approach (IRL Press, Oxford, UK, 1984) and in Newton and Graham: PCR $2^{nd}$ Edition (Springer Verlag, New York, 1997).

Additionally, methods employing DNA chips, microarrays or similar recombinant DNA technology that enables high throughput screening of DNA and polynucleotides that encode the herein described proteins or polynucleotides with high sequence homology or identity to the polynucleotides described herein. Such methods are known in the art and are described, for example, in Current Protocols in Molecular Biology, Ausebel et al (eds), John Wiley and Sons, Inc. New York (2000).

The polynucleotides and polypeptides of the present invention are proteins useful as biotechnological tools and for production of substances, specifically identified in *Corynebacterium glutamicum* ssp. *lactofermentum*. By way of example, the present inventors provide the following cited references (each of which are incorporated herein by reference) demonstrating that assays to assess the enzymatic activity of the polypeptides of the present invention are known and, as such, determination of whether a sequence falls within the scope of the present claims may be readily ascertained. These polynucleotides and polypeptides include:

1. Type I restriction modification system, M subunit comprises the amino acid sequence of SEQ ID NO:2 and is encoded by the hsdM1 gene which comprises the polynucleotide SEQ ID NO:1 (Gubler, M. et. al., EMBO J. 11:233-240, 1992);
2. Type I restriction modification system, S subunit comprises the amino acid sequence of SEQ ID NO:4 and is encoded by the hsdS1 gene which comprises the polynucleotide SEQ ID NO:3 (Gubler, M. et. al., EMBO J. 11:233-240, 1992);
3. Type I restriction modification system R subunit comprises the amino acid sequence of SEQ ID NO:6 and is encoded by the hsdR1 gene which comprises the polynucleotide SEQ ID NO:5 (Gubler, M. et. al., EMBO J. 11:233-240, 1992)
4. Type I restriction-modification system, M subunit comprises the amino acid sequence of SEQ ID NO:8 and is encoded by the hsdM2 gene which comprises the polynucleotide SEQ ID NO:7 (Gubler, M. et. al., EMBO J. 11:233-240, 1992);
5. Type I restriction-modification system, S subunit comprises the amino acid sequence of SEQ ID NO:10 and is encoded by the hsdS2 gene which comprises the polynucleotide SEQ ID NO:9 (Gubler, M. et. al., EMBO J. 11:233-240, 1992);
6. Type I restriction modification system R comprises the amino acid sequence of SEQ ID NO:12 and is encoded by the hsdR2 gene which comprises the polynucleotide SEQ ID NO:11 (Gubler, M. et. al., EMBO J. 11:233-240, 1992);
7. Type III restriction-modification system methyltransferase comprises the amino acid sequence of SEQ ID NO:14 and is encoded by the mod gene which comprises the polynucleotide SEQ ID NO:13 (Backer, O. D. and Colson, C., Gene, 97:103-107, 1991);
8. Type III restriction modification system R protein comprises the amino acid sequence of SEQ ID NO:16 and is encoded by the res gene which comprises the polynucleotide SEQ ID NO:15 (Backer, O. D. and Colson, C., Gene, 97:103-107, 1991);
9. Chaperone protein DnaK2 comprises the amino acid sequence of SEQ ID NO:18 and is encoded by a dnaK2 gene comprising SEQ ID NO:17 (Zylicz, M. and Georgopoulos, C., J. Biol. Chem. 259:8820-8825, 1984);
10. Glutamate dehydrogenase Gdh2 comprises the amino acid sequence of SEQ ID NO:20 and is encoded by a gdh2 gene comprising SEQ ID NO:19 (Bormann, E. R. et. al., Mol. Microbiol., 6:317-326, 1992; Consalvi, V. et. al. Eur. J. Biochem. 196:459-467);
11. Proline betaine uptake system ProP2 comprises the amino acid sequence of SEQ ID NO:22 and is encoded by a proP2 gene comprising SEQ ID NO:21 (Peter, H. et. al., J. Bacteriol., 180:6005-12, 1998);

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, I M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl (Anal. Biochem., 138:267-284, 1984): Tm=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C.

Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

Stringent hybridization conditions are understood to mean those conditions where hybridization, either in solution or on a solid support, occur between two polynucleotide molecules which are 70% to 100% homologous in nucleotide sequence which include 75%, 80%, 85%, 90%, 95%, 98% and all values and subranges therebetween.

Homology, sequence similarity or sequence identity of nucleotide or amino acid sequences may be determined conventionally by using known software or computer programs. To find the best segment of identity or similarity of sequences, BLAST (Altschul et. al., J. Mol. Biol. 215:403-410, 1990 and Lipman et. al., J. Mol. Biol. 215:403-410, 1990), FASTA (Lipman et. al., Science, 227:1435-1441, 1985), or Smith and Waterman (Smith and Waterman, J. Mol. Biol., 147:195-197, 1981) homology search programs can be used. To perform global alignments, sequence alignment programs such as the CLUSTAL W (Thompson et. al., Nucleic Acids Research 22:4673-4680, 1994) can be used.

The present invention also provides processes for preparing substance-producing organisms that comprise at least one polynucleotide whose expression is enhanced or attenuated. Likewise, the invention also provides processes for preparing substance-producing organisms that comprise at least on polypeptide whose activity is enhanced or attenuated. Preferably, an organism with enhanced or attenuated expression of one or more of the polypeptides and/or polynucleotides described herein will improve amino acid yield at least 1% compared to a bacterial strain not having the enhanced or attenuated expression. For the production of substances the polynucleotides described herein may be used to target expression, either by disruption to turn off or increase or enhance the expression or relative activity of the polypeptide enzymes encoded therein.

The term "enhancement" as used herein means increasing intracellular activity of one or more polypeptides in the producing organism, which in turn are encoded by the corresponding polynucleotides described herein. To facilitate such an increase, the copy number of the genes corresponding to the polynucleotides described herein may be increased. Alternatively, a strong and/or inducible promoter may be used to direct the expression of the polynucleotide, the polynucleotide being expressed either as a transient expression vehicle or homologously or heterologously incorporated into the genome. In another embodiment, the promoter, regulatory region and/or the ribosome binding site upstream of the gene can be altered to achieve the over-expression. The expression may also be enhanced by increasing the relative half-life of the messenger RNA.

In another embodiment, the enzymatic activity of the polypeptide itself may be increased by employing one or more mutations in the polypeptide amino acid sequence, which increases the activity. For example, altering the relative Km of the polypeptide with its corresponding substrate will result in enhanced activity. Likewise, the relative half-life of the polypeptide may be increased.

In either scenario, that being enhanced gene expression or enhanced enzymatic activity, the enhancement may be achieved by altering the composition of the cell culture media and/or methods used for culturing.

"Enhanced expression" or "enhanced activity" as used herein means an increase of at least 10%, 25%, 50%, 75%, 100%, 150%, 200%, 300%, 400% or 500% compared to a wild-type protein, polynucleotide, gene; or the activity and/or the concentration of the protein present before the polynucleotides or polypeptides are enhanced.

The term "attenuation" as used herein means a reduction or elimination of the intracellular activity of the polypeptides in a cell that are encoded by the corresponding polynucleotide. To facilitate such a reduction or elimination, the copy number of the genes corresponding to the polynucleotides described herein may be decreased or removed. Alternatively, a weak and/or inducible promoter may used to direct the expression of the polynucleotide, the polynucleotide being expressed either as a transient expression vehicle or homologously or heterologously incorporated into the bacterial genome. For example, the endogenous promoter or regulatory region of the gene corresponding to the isolated polynucleotides described herein may be replaced with the aforementioned weak and/or inducible promoter. Alternatively, the promoter or regulatory region may be removed. The expression may also be attenuated by decreasing the relative half-life of the messenger RNA.

In another embodiment, the enzymatic activity of the polypeptide itself may be decreased or deleted by employing one or more mutations in the polypeptide amino acid sequence, which decreases the activity or removes any detectable activity. For example, altering the relative Kd of the polypeptide with its corresponding substrate will result in attenuated activity. Likewise, a decrease in the relative half-life of the polypeptide will result in attenuated activity.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Suitable vectors for carrying *C. glutamicum* ssp. *lactofermentum* polynucleotides include those vectors which can direct expression of the gene in cells as known in the art. One embodiment of the present invention is whereby the vectors contain an inducible or otherwise regulated expression system whereby the *C. glutamicum* ssp. *lactofermentum* polynucleotides may be expressed under certain conditions and not expressed under other conditions. Furthermore, in another embodiment of the invention, the *C. glutamicum* ssp. *lactofermentum* polynucleotides can be constitutively expressed. Examples of such vectors and suitable cells in which they can be introduced are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York, 2000.

Methods of introducing *C. glutamicum* ssp. *lactofermentum* polynucleotides or vectors containing the *C. glutamicum* ssp. *lactofermentum* polynucleotides include electroporation, conjugation, calcium-mediated transfection, infection with bacteriophage and other methods known in the art. These and other methods are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York (2000).

The microorganisms that can be used in the present invention preferably have the ability to produce amino acids, preferably L-amino acids, from a suitable carbon source, preferably carbon sources such as methanol, glucose, sucrose, lactose, fructose, maltose, molasses, starch, cellulose glycerol or ethanol. The microorganisms can be *Corynebacterium* bacteria, preferably *Corynebacterium glutamicum* ssp. *lactofermentum*.

Suitable culture conditions for the growth and/or production of *C. glutamicum* polynucleotides are dependent on the cell type used. Likewise, culturing cells that contain attenuated or enhanced expression of the *C. glutamicums* polynucleotides or polypeptides, as described herein, may be cultured in accordance with methods known in the art. Examples of culture conditions for various cells is described in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, (Eds.), John Wiley and Sons, Inc., 2000; and Cells: A Laboratory Manual (Vols. 1-3), Spector et al, (Eds.), Cold Spring Harbor Laboratory Press, Cold Spring Harbor, N.Y., (1988).

Following culturing the polypeptide or protein products, which are encoded by the *C. glutamicuin* polynucleotides, may be purified using known methods of protein purification. These methods include high performance liquid chromatography (HPLC), ion-exchange chromatography, size exclusion chromatography; affinity separations using materials such as beads with exposed heparin, metals, or lipids; or other approaches known to those skilled in the art. These and other methods of protein purification are disclosed in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, eds., John Wiley and Sons, Inc., 2000 and Protein Purification, Scopes and Cantor, (Eds.), Springer-Verlag, (1994). Likewise, the amino acids produced may be purified by methods known in the art using similar chromatography devices.

The invention also provides antibodies that bind to the polypeptides of the present invention. Antibodies binding to the polypeptides can be either monoclonal or polyclonal, preferably the antibodies are monoclonal. Methods for obtaining antibodies that bind to the polypeptides are known in the art and are described, for example, in Harlow and Lane, Antibodies: A Laboratory Manual, Cold Spring Harbor Laboratory Press, Cold Spring Harbor, N.Y. (1988).

Having generally described this invention, a further understanding can be obtained by reference to certain specific examples which are provided herein for purposes of illustration only, and are not intended to be limiting unless otherwise specified.

EXAMPLES

General DNA manipulation was performed according to previously described methods (Sambrook et. al. (1989) "Molecular Cloning: A Laboratory Manual/Second Edition", Cold Spring Harbor Laboratory Press). Whole genome sequencing was performed using random shotgun method as described by Fleischman R. D. et. al. (Science, 269:496-512, 1995).

Example 1

Construction of genomic libraries of *C. glutamicum* ssp. *lactofermentum* Genomic DNA of a wild type strain *C. glutamicum* ssp. *lactofermentum* ATCC 13869 was isolated as described in (Y. Usuda et. al., Microbiology, 142:3347-3354, 1996). The genomic DNA was sheared and fragmentized by sonication. The resultant fragments in the 1- to 2-kilo base pairs (kbp) size range were purified by gel electrophoresis through 1% agarose gel, followed by recovery using the QIAquick Gel Extraction kit (Qiagen K. K., Tokyo, Japan). The recovered fragments were blunted, phosphorylated, and ligated to the high-copy number vector pUC 118 treated with HindII and bacterial alkaline phosphatase (Takara Shuzo, Kyoto, Japan), using Blunting Kination Ligation Kit (Takara Shuzo). This was designated pUC 118 library.

To get larger fragments, the genomic DNA was digested with varying amounts of Sau3AI. One fraction containing the greatest mass of 30-40 kbp range was selected by analyzing an aliquot of each fraction on 0.8% agarose gel electrophoresis. Another aliquot of the fraction was dephosphorylated with calf intestine alkaline phosphatase (New England Biolabs, MA, USA) and ligated into the BamHI site of cosmid vector SuperCos 1 (Stratagene, CA, USA) and followed by packging in λ phage. This library composed of 30-40 kbp range fragments was designated the cosmid library.

Example 2

DNA Sequencing and Sequence Assembly

The pUC118 library were introduced into *Escherichia coli* strain DH5α and plated on Luria-Bertani medium containing 100 μg/ml ampicillin and 40 μg/ml 5-bromo-4-chloro-3-indolyl-α-D-galactoside (X-Gal). The white colonies were picked up and cultured in Luria-Bertani (LB) medium containing 100 μg/ml ampicillin. The individual colony was cultured in the well of the 96 deep-well plates, and the plasmids were isolated using QIAprep Turbo Kit (Qiagen). The DNA fragments inserted into pUC118 were sequenced using a M13 reverse primer. The shotgun sequencing was performed with the BigDye terminators and 3700 DNA analyzer (Applied Biosystems Japan, Tokyo, Japan). Approximately 55,000 samples from pUC118 library corresponding to coverage of over 8-fold to the genome size were analyzed and the sequences were assembled by Phred/Phrap software (CodonCode, MA, USA). From the assemble results, the clones which assumed to link the contigs were picked up and sequenced by M13 forward primer, M3. The re-assembly by Phrad/Phrap with Repeat Masker program that exclude the repeat sequences yielded 52 contigs over 5 kb in length.

As for cosmid library, the packaged particles were introduced into E. coli strain XL1-Blue MR and selected on LB plates containing 25 μg/ml kanamycin. Approximately 900 clones corresponding to coverage of over 10-fold were sequenced using both T3 and T7 universal primers. Based on the both end-sequence data from the cosmid library and 52 contig sequences from the plasmid library, direct linkage between contigs were estimated by using CAT (Clustering and Alignment Tools) software (Hitachi Ltd., Tokyo, Japan) and linking cosmid clones were selected from the library. To fill gap region between contigs, sequences of inserted fragments of the selected clones were determined by using primer-walking method. The further remaining gap regions between contigs, C. glulamicum ssp. lactofermentum genomic DNA were amplified by PCR using primers designed by the end-sequences of contigs, and the amplified products were sequenced directly by primer walking. The repeat sequences confirmed by resequening of PCR fragments amplified from appropriate cosmid clones. Several regions were determined by sequencing in only one direction because of postulated secondary structures or high GC contents.

By this research, the genome of C. glutamicum ssp. lactofermentum was found to be a single circular form with the size of 3,272,733 bases and GC content of 54.2%.

Example 3

Sequence Analysis and Annotation

Genome sequence analysis was managed by using the Genome Gambler software (Sakiyama, T. et. al., Biosci. Biotechnol. Biochem., 64: 670-673, 2000). The prediction of the protein-coding regions was performed by Glimmer 2.0 program (Delcher A. L. et al., Nucleic Acids Res., 27:4636-4641, 1999), using a default condition with the sequence, 5'-AAA-GAGG-3', as the Shine-Dalgarno sequence (Amador, E. et. al., Microbiology, 145:915-924, 1999). The 3,545 open reading frames (ORFs) were extracted as putative protein-coding genes. The genome sequence of C. glutamicum wild type strain in DDBJ/EMBL/GenBank (BA000036) was used as a reference. To determine the strain-specific genes, following successive homology searches at nucleotide level were executed. (1) The homology search using the BLASTN program (Altschul et. al., J. Mol. Biol., 215:403-410, 1990) with nucleotide sequences of ORF of each strain as queries against all ORF sequences was performed. From the search results, the ORFs from genomes of two strains with less than 100 alignment length and with the score less than 100 were selected as candidates for the next steps. (2) The homology search using the BLASTN program with candidate ORF sequences as queries against a whole genome sequence of the other strain. From homology search results, the ORFs with less than 100 alignment length and with the score less than 100 were extracted as candidates for the next steps. The ORFs with less than 300 bp in length were excluded from the candidates for the strain-specific ORFs. (3) To confirm that these candidates for strain-specific ORF does not show homology at amino acid sequence level, amino acid sequences were subjected to homology search using FASTA program (Lipman et. al., Science, 227:1435-1441, 1985) against all ORFs of the other strain. The ORFs that did not show homology to any amino acid sequences of the other strain were treated as the strain-specific ORFs. To estimate the function of the strain-specific ORFs, homology search of amino acid sequences were executed using the BLASTP program against non-redundant amino acid sequence database from GenBank.

As a result of homology search (1), 636 ORF were obtained as candidates for C. glutamicum ssp. lactofermentum strain specific ORFs. By the search (2), 424 ORFs were extracted as candidates of C. glutamicum ssp. lactofermentum strain specific ORFs from 636 ORFs used as query sequences. At this step, the ORFs with less than 300 bp in length were excluded and 220 ORFs were selected as candidates for strain specific ORF in C. glutamicum ssp. lactofermentum. The homology search (3) revealed 12 ORFs showed significant homology with ORFs in C. glutamicum at amino acid sequence level. Finally, 208 ORFs were selected as the C. glutamicum ssp. lactofermentum strain-specific gene. From the BLAST search results against non-redundant protein sequences, careful assignment of gene function was performed to identify the genes encoding the useful genes in the biotechnology field. The two sets of type I restriction-modification system (hsdM1-hsdS 1-hsdR1 and hsdM2-hsdS2-hsdR2) and one of type III restriction-modification system (mod-res). The second dnaK gene (dnaK2) encoding molecular chaperone protein, the second glutamate dehydrogenase gene (gdh2), and the second proline betaine uptake system gene (proP2) were identified.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide encoding a protein comprising the amino acid sequence of SEQ ID NO:22.

2. A vector comprising the isolated polynucleotide of claim 1.

3. An isolated host cell comprising the isolated polynucleotide of claim 1.

4. The host cell of claim 3, which is a *Corynebacterium*.

5. A method of making the protein comprising the amino acid sequence of SEQ ID NO: 22 comprising:
   A) culturing the host cell of claim 3 for a time and under conditions suitable for expression of said protein; and
   B) collecting said protein.

6. A method of producing an L-amino acid comprising:
   A) culturing the host cell of claim 3 for a time and under conditions suitable for producing the L-amino acid; and
   B) collecting the L-amino acid.

7. The method of claim 6, wherein said host cell is a *Corynebacterium*.

8. An isolated polynucleotide comprising the nucleotide sequence of SEQ ID NO:21.

9. A vector comprising the isolated polynucleotide of claim 8.

10. An isolated host cell comprising the isolated polynucleotide of claim 8.

11. The host cell of claim 10, which is a *Corynebacterium*.

12. A method of making the protein encoded by the nucleotide sequence of SEQ ID NO:21 comprising:
    A) culturing the host cell of claim 10 for a time and under conditions suitable for the expression of the polynucleotide; and
    B) collecting said protein.

13. A method of producing an L-amino acid comprising:
    A) culturing the host cell of claim 10 for a time and under conditions suitable for producing the L-amino acid; and
    B) collecting the L-amino acid.

14. The method of claim 13, wherein said host cell is a *Corynebacterium*.

15. An isolated polynucleotide, which hybridizes under stringent conditions to the isolated polynucleotide of claim 8, wherein said stringent conditions are hybridization in 50% formamide, 1M NaCl, and 1% SDS at 37° C., and a wash in 0.1×SSC at 60° C. to 65° C., and wherein said polynucleotide encodes a protein having proline/betaine transporter activity.

16. A vector comprising the isolated polynucleotide of claim 15.

17. A isolated host cell comprising the isolated polynucleotide of claim 15.

18. A method of making a protein having proline/betaine transporter activity comprising:
    A) culturing the host cell of claim 17 for a time and under conditions suitable for the expression of the polynucleotide to produce the protein; and
    B) collecting said protein.

19. A method of producing an L-amino acid comprising:
    A) culturing the host cell of claim 17 for a time and under conditions suitable for producing an L-amino acid; and
    B) collecting the L-amino acid.

20. The method of claim 19, wherein said host cell is a *Corynebacterium*.

21. An isolated polynucleotide, which is at least 95% identical to the polynucleotide of claim 8, and wherein said polynucleotide encodes a protein having proline/betaine transporter activity.

22. A vector comprising the isolated polynucleotide of claim 21.

23. A isolated host cell comprising the isolated polynucleotide of claim 21.

24. A method of making a protein having proline/betaine transporter activity comprising:
    A) culturing the host cell of claim 23 for a time and under conditions suitable for the expression of the polynucleotide to produce the protein; and
    B) collecting said protein.

25. A method of producing an L-amino acid comprising:
    A) culturing the host cell of claim 23 for a time and under conditions suitable for producing the L-amino acid; and
    B) collecting the L-amino acid.

26. The method of claim 25, wherein said host cell is a *Corynebacterium*.

27. The host cell of claim 17, which is a *Corynebacterium*.

28. The host cell of claim 23, which is a *Corynebacterium*.

* * * * *

SEQUENCE LISTING

```
<160> NUMBER OF SEQ ID NOS: 22

<210> SEQ ID NO 1
<211> LENGTH: 1569
<212> TYPE: DNA
<213> ORGANISM: Corynebacterium glutamicum ssp. Lactofermentum

<400> SEQUENCE: 1
atgattacag gcactctcaa gtcccaggta gacaaaatct gggacacttt ctggtccggt      60
ggcatctcca accccatctc cgtgattgaa cagttcacct atctgctgtt catgcgtcag     120
ctcgatgagc gccaggccag caatgatttc cagcgcaccc tcggcgtcga ccctccacc     180 gcggacatct tcgataagga gcaccaacac ctgcgctggc gtaatctcat ggagatttcc     240
```

-continued

```
gacggagcga agcgccggaa gatcatcgtc gatgaagttt tccctttcct ccgcaccctc      300
ggcggcagcg gcttcgcgca gcatatgagc aacgccagct tcggcatcga aaccccgcc       360
accctcatca gcgtgatgaa gcaggtcaac gacctgaagt tcgccaacaa ggacattgct      420
ggcgacctct acgagtacat gctgtccaag ctcaccacct caggcaccaa cgggcagttc      480
cgcaccccga gccacatcat cgacctcatg gtcgaactca tgcgcccgtc ccccacccaa      540
cgggtcatcg acccggcctc cggcaccgcc ggtttcctcg tggcggcttc cgaatggact      600
cgccgccatc acgcggagga gcttctcgac gcccgcctgc gccagcgcta caacgagtcc      660
ggtctgaccg gcttcgactt cgactccacg atggtgcgca tcgccgcgat gaacatgttc      720
atgcacggct tcgaggaccc gaacatcagc taccgcgatg cactccagca ggtcccccac      780
gaggatcagg aggcctacga catcgtcctg gccaacccac ccttcgccgg cagcatcgac      840
gaatccagca tggaccccggc gctgtccaac ctggtcagct cgaagaagac ggaactgctg     900
tttgtcgctc gcttcctcac cctgctcaaa ccaggtggcc gcgccgctgt tattgtcccc      960
gaaggtgtgc tcttcggctc caccaaggca cataagcagc tgcgtaagca cctgctcgat     1020
gagcagcgtc tcgatgccgt gatcaagctt ccctccggtg cgttcaaacc ctattccggt     1080
gtgtccactg caattctgtg cttcacccgc actgaccgcg gcagtaccga ggacgtgtgg     1140
ttctacgagg tcaccgccga tggtttctca ttggatgata agcgcacgcc gcttctcgcc     1200
gctcacctgc tcggtcccac tcctaccgtg cgcccgcgcg actcggagct gccgatgac     1260
aatcccgatg cagccagcct taccgccgac cagcacgagt tgaataacct gcccgacgtg     1320
ctcacccgtt ggcaggaaca caccggtgcc gagcgcaagc gtgctcgcac tgaacagtcc     1380
ttcaccgtgc ccgctgagga gatccgcgag gccgactatg acctctcgat gaaccggtac     1440
aaggagatcg tcttcggcgc cgaagacacc cgggacccgt ggagatcat tgctgagatc     1500
aaagaattgg acgccgagat tgcggcgggg atgggcaagc tggaagccat gctgcaggag     1560
ggaaagtag                                                             1569
```

<210> SEQ ID NO 2
<211> LENGTH: 522
<212> TYPE: PRT
<213> ORGANISM: Corynebacterium glutamicum ssp. Lactofermentum

<400> SEQUENCE: 2

```
Met Ile Thr Gly Thr Leu Lys Ser Gln Val Asp Lys Ile Trp Asp Thr
1               5                   10                  15

Phe Trp Ser Gly Gly Ile Ser Asn Pro Ile Ser Val Ile Glu Gln Phe
            20                  25                  30

Thr Tyr Leu Leu Phe Met Arg Gln Leu Asp Glu Arg Gln Ala Ser Asn
        35                  40                  45

Asp Phe Gln Arg Thr Leu Gly Val Asp Pro Ser Thr Ala Asp Ile Phe
    50                  55                  60

Asp Lys Glu His Gln His Leu Arg Trp Arg Asn Leu Met Glu Ile Ser
65                  70                  75                  80

Asp Gly Ala Lys Arg Arg Lys Ile Ile Val Asp Glu Val Phe Pro Phe
                85                  90                  95

Leu Arg Thr Leu Gly Gly Ser Gly Phe Ala Gln His Met Ser Asn Ala
            100                 105                 110

Ser Phe Gly Ile Glu Asn Pro Ala Thr Leu Ile Ser Val Met Lys Gln
        115                 120                 125
```

```
Val Asn Asp Leu Lys Phe Ala Asn Lys Asp Ile Ala Gly Asp Leu Tyr
130                 135                 140

Glu Tyr Met Leu Ser Lys Leu Thr Thr Ser Gly Thr Asn Gly Gln Phe
145                 150                 155                 160

Arg Thr Pro Ser His Ile Ile Asp Leu Met Val Glu Leu Met Arg Pro
                165                 170                 175

Ser Pro Thr Gln Arg Val Ile Asp Pro Ala Ser Gly Thr Ala Gly Phe
            180                 185                 190

Leu Val Ala Ala Ser Glu Trp Thr Arg Arg His His Ala Glu Glu Leu
        195                 200                 205

Leu Asp Ala Arg Leu Arg Gln Arg Tyr Asn Glu Ser Gly Leu Thr Gly
210                 215                 220

Phe Asp Phe Asp Ser Thr Met Val Arg Ile Ala Ala Met Asn Met Phe
225                 230                 235                 240

Met His Gly Phe Glu Asp Pro Asn Ile Ser Tyr Arg Asp Ala Leu Gln
                245                 250                 255

Gln Val Pro His Glu Asp Gln Glu Ala Tyr Asp Ile Val Leu Ala Asn
            260                 265                 270

Pro Pro Phe Ala Gly Ser Ile Asp Glu Ser Ser Met Asp Pro Ala Leu
        275                 280                 285

Ser Asn Leu Val Ser Ser Lys Lys Thr Glu Leu Leu Phe Val Ala Arg
290                 295                 300

Phe Leu Thr Leu Leu Lys Pro Gly Gly Arg Ala Ala Val Ile Val Pro
305                 310                 315                 320

Glu Gly Val Leu Phe Gly Ser Thr Lys Ala His Lys Gln Leu Arg Lys
                325                 330                 335

His Leu Leu Asp Glu Gln Arg Leu Asp Ala Val Ile Lys Leu Pro Ser
            340                 345                 350

Gly Ala Phe Lys Pro Tyr Ser Gly Val Ser Thr Ala Ile Leu Cys Phe
        355                 360                 365

Thr Arg Thr Asp Arg Gly Ser Thr Glu Asp Val Trp Phe Tyr Glu Val
370                 375                 380

Thr Ala Asp Gly Phe Ser Leu Asp Asp Lys Arg Thr Pro Leu Leu Ala
385                 390                 395                 400

Ala His Leu Leu Gly Pro Thr Pro Thr Val Arg Pro Arg Asp Ser Glu
                405                 410                 415

Leu Ala Asp Asp Asn Pro Asp Ala Ala Ser Leu Thr Ala Asp Gln His
            420                 425                 430

Glu Leu Asn Asn Leu Pro Asp Val Leu Thr Arg Trp Gln Glu His Thr
        435                 440                 445

Gly Ala Glu Arg Lys Arg Ala Arg Thr Glu Gln Ser Phe Thr Val Pro
450                 455                 460

Ala Glu Glu Ile Arg Glu Ala Asp Tyr Asp Leu Ser Met Asn Arg Tyr
465                 470                 475                 480

Lys Glu Ile Val Phe Gly Ala Glu Asp Thr Arg Asp Pro Leu Glu Ile
                485                 490                 495

Ile Ala Glu Ile Lys Glu Leu Asp Ala Glu Ile Ala Ala Gly Met Gly
            500                 505                 510

Lys Leu Glu Ala Met Leu Gln Glu Gly Lys
        515                 520

<210> SEQ ID NO 3
<211> LENGTH: 1173
<212> TYPE: DNA
```

<213> ORGANISM: Corynebacterium glutamicum ssp. Lactofermentum

<400> SEQUENCE: 3

```
atgagcagtg ttaatgagtg gccgatggtg aagcttgggg atatccaacg caaagtttca      60
tcgatcaatc ccgctaagtc tccagatcaa gaattttctt tatacagcat ccccgcttat     120
gatgcgggcg cccctgagaa agccttaggt agcgcgatta aatcaaacaa gattgagcta     180
cagccaggcg ataccttgtt gtccaagatc gtccctcata tccgccgatc ttggatcgtt     240
gacgaacatg aaacttcctc cattggtagc tcagagtgga ttgtttatca ggatgaccgt     300
ttagattctc gttttctccg taactttttt ctatcagact attttcatgc ccaattcatg     360
caaacagtcg caggagtcgg cggatctttg aatcgcgcgc ggccagctgc tgttgcccaa     420
atatcaattc ctatccccc acggcctgag cagcagcgca tcgccgaaat ccttgacgtt      480
acccagcaac agttcgatct tttgaaggcc aggaaaacac atctgtcttc tctaagaact     540
gggctcgttg accagtttct cgaggctgat gaccgagaga ctcttcccct gaaggaaatt     600
gcagaaattc agtcgggtat caccaaaggc cgtagagttc gaaatggcga aattttaact     660
gaaactgctt acatggcggt ttccaatgtc aaagatggac accttaatct cgggacagtg     720
aaaaccatcc ggcgacaga agccgagatc acgcgattcc gcctgaaagc tggggatgtc     780
ctgctgaccg aagtggcga tcccgacaaa cttggcagag cacggtctg gcgtgatgaa      840
atcgagcctt gtctgcatca aaaccacatt ttccgtgttc gattaccgga agattcccga     900
ttcaccccgg aagtcctcat ggccatgctc tccaccaaac aagctcgcgc ctatttcttc     960
cgttccgcca aacagacaac cggtatcgct tcaatcaata agacccaatt gtccgcagtc    1020
cctgtgccaa tcttgacgga ttccgagatc gccaagctgt cagaggctct cacccagata    1080
gacatactct ctagttacat agaaaaacgt cgtatagcaa ccgaaagcct tcaccgcgcc    1140
ctctctaccc gtgctttcgc aggtcagctt taa                                 1173
```

<210> SEQ ID NO 4
<211> LENGTH: 390
<212> TYPE: PRT
<213> ORGANISM: Corynebacterium glutamicum ssp. Lactofermentum

<400> SEQUENCE: 4

```
Met Ser Ser Val Asn Glu Trp Pro Met Val Lys Leu Gly Asp Ile Gln
1               5                   10                  15

Arg Lys Val Ser Ser Ile Asn Pro Ala Lys Ser Pro Asp Gln Glu Phe
            20                  25                  30

Ser Leu Tyr Ser Ile Pro Ala Tyr Asp Ala Gly Ala Pro Glu Lys Ala
        35                  40                  45

Leu Gly Ser Ala Ile Lys Ser Asn Lys Ile Glu Leu Gln Pro Gly Asp
    50                  55                  60

Thr Leu Leu Ser Lys Ile Val Pro His Ile Arg Arg Ser Trp Ile Val
65                  70                  75                  80

Asp Glu His Glu Thr Ser Ser Ile Gly Ser Ser Glu Trp Ile Val Tyr
                85                  90                  95

Gln Asp Asp Arg Leu Asp Ser Arg Phe Leu Arg Asn Phe Phe Leu Ser
            100                 105                 110

Asp Tyr Phe His Ala Gln Phe Met Gln Thr Val Ala Gly Val Gly Gly
        115                 120                 125

Ser Leu Asn Arg Ala Arg Pro Ala Ala Val Ala Gln Ile Ser Ile Pro
    130                 135                 140
```

```
Ile Pro Pro Arg Pro Glu Gln Gln Arg Ile Ala Glu Ile Leu Asp Val
145                 150                 155                 160

Thr Gln Gln Gln Phe Asp Leu Leu Lys Ala Arg Lys Thr His Leu Ser
                165                 170                 175

Ser Leu Arg Thr Gly Leu Val Asp Gln Phe Leu Glu Ala Asp Asp Arg
            180                 185                 190

Glu Thr Leu Pro Leu Lys Glu Ile Ala Glu Ile Gln Ser Gly Ile Thr
        195                 200                 205

Lys Gly Arg Arg Val Arg Asn Gly Glu Ile Leu Thr Glu Thr Ala Tyr
    210                 215                 220

Met Ala Val Ser Asn Val Lys Asp Gly His Leu Asn Leu Gly Thr Val
225                 230                 235                 240

Lys Thr Ile Pro Ala Thr Glu Ala Glu Ile Thr Arg Phe Arg Leu Lys
                245                 250                 255

Ala Gly Asp Val Leu Leu Thr Glu Gly Gly Asp Pro Asp Lys Leu Gly
            260                 265                 270

Arg Gly Thr Val Trp Arg Asp Glu Ile Glu Pro Cys Leu His Gln Asn
        275                 280                 285

His Ile Phe Arg Val Arg Leu Pro Glu Asp Ser Arg Phe Thr Pro Glu
    290                 295                 300

Val Leu Met Ala Met Leu Ser Thr Lys Gln Ala Arg Ala Tyr Phe Phe
305                 310                 315                 320

Arg Ser Ala Lys Gln Thr Thr Gly Ile Ala Ser Ile Asn Lys Thr Gln
                325                 330                 335

Leu Ser Ala Val Pro Val Pro Ile Leu Thr Asp Ser Glu Ile Ala Lys
            340                 345                 350

Leu Ser Glu Ala Leu Thr Gln Ile Asp Ile Leu Ser Ser Tyr Ile Glu
        355                 360                 365

Lys Arg Arg Ile Ala Thr Glu Ser Leu His Arg Ala Leu Ser Thr Arg
    370                 375                 380

Ala Phe Ala Gly Gln Leu
385                 390

<210> SEQ ID NO 5
<211> LENGTH: 3603
<212> TYPE: DNA
<213> ORGANISM: Corynebacterium glutamicum ssp. Lactofermentum

<400> SEQUENCE: 5
atgacacaag cgatccccca gaccaacttc ggattcgtgg acgtgtgtg gccagcgctg      60 ctcaacgact gccgccaagc cgagcgcagc gcgctctcca atccggtggt ctcctgtttc    120
tactctcgcc gtgtcctcga acgcgtcgtc cgccacatct gggaattccg gaagctcggc    180
cccatcggcg atgacagcac gttcggccgt ctcaaagacg atcgcttcat aggtgtctcc    240
accaccctcc aactagacaa aatgcattac attcggctgc gcggcaacga cgccgtccac    300
gagggaaagc agcccatcac accgcagatc gccacaaagg tgatcatgca gcttttcgac    360
gtcctcagct gggccactgc acgacactcc acgcatcccg aagcacaacc cgcggccccg    420
ttcgatccgc agttcctcaa ggcggctccc gcccaaccac ccgtcaaccg agcccaactg    480
aagaaactgg ctgcagacct cgaggccaaa gacgctgaac ttaatgagac tgctctgctt    540
ctcgacgaag ccgagcagga acgcctcgcg caggcagaaa agcacgctga ggagcgtgca    600
ctcttcgccg cccgcagcct cgaaaccgag gagaaacgcg ccgccaccga ggccgaactc    660
attgctgccc aagaagaact caagcgtgtc aacgctgagc gcgacgccga gatcgagcgc    720
```

```
cttcgtgcgg agctgcgtga tgagctggcc aagaaggctg gcagcggagt ggcccccgact    780
ctcccaccga cgatcagcga agcgcagacc cggcgtgatc tcatcgatcc gatgctcgcc    840
attgccagct tccacctcgg ccagaatgcc accgtcgagt atcccgtcaa gggcatgccg    900
atctcggcag aaagccctca cggcaacggt tttgccgatt acgtgctctg ggacgatgac    960
ggtcagcccc tcgccgtcgt ggaagccaag cgatccagcg ctaacctgtc cgacggagcc   1020
gtccaggccc gcctctacgc cgactgcctc gcagccaagt tcggtcggcg tcccatcatt   1080
ttctgcacca acgacatctc cattgagatg accgacgacg ccgccagtct tcccggttct   1140
ggtcgtgggt atcccacccg tcaagtggag ggctacccat ccgcgggaca actccggcag   1200
atgatcaacc gtcgcaccac ccgcctgcca ctggcagatg ccgtggtgga cccgcagatc   1260
gccggccgtg actaccagca ggaaatgatc cggcgtgtca ccgaatcctt cgaacacgac   1320
ctgaatcgtc gcgcgctgct ggtcatggcc actggtaccg gcaagacacg tgtcgctatc   1380
gccacctcca agttgctgcg tgaatccaac tgggtgggca acgtactttt cctcgctgac   1440
cgcacagcac tcgtcgacca ggctcacgac aacttcgtcg accattatcc tgaatcggcg   1500
ccggtgaacc tgctcagcga tccagacggc gtcggcgggg tctacatctc cacgtatcag   1560
acgatgatga cctgatcaa cgacgacggc gagacgcccg caaagttccg ccctttcgac   1620
ttcgatctca tcatcatcga cgaggcacac cgctcgatct atcaccgctt caagcgcatc   1680
ctcgactact tcgatgccta cgtcctcgga ctgaccgcca ctccgaagtc ggaggttcac   1740
cgcaacactt atcagctctt cgacatcgac gggaagaacc ccaccggttc ctacacccctc   1800
gaacaggccg ttgaagacaa gtacctggtg ccaccccagg tcatcacaca ggactcgctc   1860
ttcctgcgca gcggtgtccg ctacgaggac ctagacgttg acgagcagca gcgctgggat   1920
gaggccgagt ggggcacgga tgaagacggc aacccactgg acccacccga cggcgtctca   1980
gccgccgaga tcaactcgcg gctctacaac cgcgacacca tccgcaaggt gctgaagacg   2040
ctggtcaccg aaggcatcaa ggtcgagggt ggcgaccggt tgggcaagac catcatcttc   2100
gcccgcaccc agaagcacgc cagcctcatt aaggaggagt tcgaccgtca cttcccgctc   2160
tacgccggtg agaacgcctc cgtgatcacc cactccaccc gctacgctgc tgctgagctc   2220
aaacgcttta agaaccccac cagcggcctc aacgtcgcca tcagcgtcga catgcttgat   2280
accggcgtcg acgtccccga agtcgttaac ctcatcttct tcaagcccgt ctactcatcc   2340
acaaagttct ggcagatgat gggacgcggc acccgcctgc gcctgaatct cttcggcgac   2400
ggaatccaca aggacaagtt ccgggtctttt gacttctgcg gcaacgcacg attcttcatg   2460
gagcagcagc ccgaagatcc gggcataggg cgccaggtgt cgctgtcgga aagcttttc   2520
ctcagccggg cctcgctggt cgcccagctc gatcagcgca acgacgtacc ggcagacctt   2580
cgcatcgaac tggctgctga ccttcacaag tcagtcagcc agattccccc gacgcacatt   2640
caggtccgac ctctggaccg tcctattctc gagtattatc agcaagccga ggcatggaaa   2700
acggtgacgg aggacgacgt cgagaagctc ggcgaccaca tcgccagctt gccgatgaaa   2760
acgatggacg agaaggaatc cgccaagcgc tttgaccttc tcatcctgca actccagctc   2820
gggctactga acgaggacac ttcgtgggcg aagaaccgac agcgagtaga aaaaatcgcc   2880
gacgagctac ttactgtctc tgagaacctc ccatttgtcg ctgcagcctc caagactctg   2940
gaggcactgc tggattccga atggtgggaa ggcgtcacaa ttcccgagct ggaaaaggtc   3000
cgtcgcgaga tccgggatct cgtcgagttt gtgccgcgtc acaaacgcca ggtcgtggtc   3060
```

-continued

```
ctcgacgtgg aggacgaatt cggtgacatc gccgaggtgg acctacccgt tgagcacgcc    3120
gctgtcgggg tcaacgtcag ccgtgtcgag gaagagctcc gtgcctccct agacgatcat    3180
cgcgattcct tggcgatgca gaagctccgc actgctcgac cgttaactga atctgacgtc    3240
gaggacttgg aaacaatggt cgcggatacc ggcctggagg gggttgacga ggttcgggag    3300
agcctgggcg gcgacactat ccctgcgttc gttcgtcgtc tcgttggtct tgacgaggaa    3360
acaatgcgtg cagagttcgc agacttgctg gaaggctcaa cattgactgc caaccagatc    3420
agtttcatcc gccatgtcat caaggttctc gtgaacaacg gcgggttgac gatgcaggaa    3480
gccttcgacg agtccttcta cccctacggc cgtgtttctg atttgttcca ggacaaccag    3540
gcggtggtgc tcgatcttaa gagtcgccta gaccggatta atgcgaccgc agacgtcagc    3600
tga                                                                  3603
```

<210> SEQ ID NO 6
<211> LENGTH: 1200
<212> TYPE: PRT
<213> ORGANISM: Corynebacterium glutamicum ssp. Lactofermentum

<400> SEQUENCE: 6

```
Met Thr Gln Ala Ile Pro Gln Thr Asn Phe Gly Phe Val Gly Arg Val
1               5                   10                  15

Trp Pro Ala Leu Leu Asn Asp Cys Arg Gln Ala Glu Arg Ser Ala Leu
            20                  25                  30

Ser Asn Pro Val Val Ser Cys Phe Tyr Ser Arg Arg Val Leu Glu Arg
        35                  40                  45

Val Val Arg His Ile Trp Glu Phe Arg Lys Leu Gly Pro Ile Gly Asp
    50                  55                  60

Asp Ser Thr Phe Gly Arg Leu Lys Asp Asp Arg Phe Ile Gly Val Ser
65                  70                  75                  80

Thr Thr Leu Gln Leu Asp Lys Met His Tyr Ile Arg Leu Arg Gly Asn
                85                  90                  95

Asp Ala Val His Glu Gly Lys Gln Pro Ile Thr Pro Gln Ile Ala Thr
            100                 105                 110

Lys Val Ile Met Gln Leu Phe Asp Val Leu Ser Trp Ala Thr Ala Arg
        115                 120                 125

His Ser Thr His Pro Glu Ala Gln Pro Ala Ala Pro Phe Asp Pro Gln
    130                 135                 140

Phe Leu Lys Ala Ala Pro Ala Gln Pro Pro Val Asn Arg Ala Gln Leu
145                 150                 155                 160

Lys Lys Leu Ala Ala Asp Leu Glu Ala Lys Asp Ala Glu Leu Asn Glu
                165                 170                 175

Thr Ala Leu Leu Leu Asp Glu Ala Glu Gln Glu Arg Leu Ala Gln Ala
            180                 185                 190

Glu Lys His Ala Glu Glu Arg Ala Leu Phe Ala Ala Arg Ser Leu Glu
        195                 200                 205

Thr Glu Glu Lys Arg Ala Ala Thr Glu Ala Glu Leu Ile Ala Ala Gln
    210                 215                 220

Glu Glu Leu Lys Arg Val Asn Ala Glu Arg Asp Ala Glu Ile Glu Arg
225                 230                 235                 240

Leu Arg Ala Glu Leu Arg Asp Glu Leu Ala Lys Lys Ala Gly Ser Gly
                245                 250                 255

Val Ala Pro Thr Leu Pro Pro Thr Ile Ser Glu Ala Gln Thr Arg Arg
            260                 265                 270
```

```
Asp Leu Ile Asp Pro Met Leu Ala Ile Ala Ser Phe His Leu Gly Gln
        275                 280                 285

Asn Ala Thr Val Glu Tyr Pro Val Lys Gly Met Pro Ile Ser Ala Glu
    290                 295                 300

Ser Pro His Gly Asn Gly Phe Ala Asp Tyr Val Leu Trp Asp Asp
305                 310                 315                 320

Gly Gln Pro Leu Ala Val Val Glu Ala Lys Arg Ser Ser Ala Asn Leu
                325                 330                 335

Ser Asp Gly Ala Val Gln Ala Arg Leu Tyr Ala Asp Cys Leu Ala Ala
            340                 345                 350

Lys Phe Gly Arg Arg Pro Ile Ile Phe Cys Thr Asn Gly His Leu Ile
        355                 360                 365

Glu Met Thr Asp Asp Ala Ala Ser Leu Pro Gly Ser Gly Arg Gly Tyr
    370                 375                 380

Pro Thr Arg Gln Val Glu Gly Tyr Pro Ser Ala Gly Gln Leu Arg Gln
385                 390                 395                 400

Met Ile Asn Arg Arg Thr Thr Arg Leu Pro Leu Ala Asp Ala Val Val
                405                 410                 415

Asp Pro Gln Ile Ala Gly Arg Asp Tyr Gln Gln Glu Met Ile Arg Arg
            420                 425                 430

Val Thr Glu Ser Phe Glu His Asp Leu Asn Arg Arg Ala Leu Leu Val
        435                 440                 445

Met Ala Thr Gly Thr Gly Lys Thr Arg Val Ala Ile Ala Thr Ser Lys
    450                 455                 460

Leu Leu Arg Glu Ser Asn Trp Val Gly Asn Val Leu Phe Leu Ala Asp
465                 470                 475                 480

Arg Thr Ala Leu Val Asp Gln Ala His Asp Asn Phe Val Asp His Tyr
                485                 490                 495

Pro Glu Ser Ala Pro Val Asn Leu Leu Ser Asp Pro Asp Gly Val Gly
            500                 505                 510

Gly Val Tyr Ile Ser Thr Tyr Gln Thr Met Met Ser Leu Ile Asn Asp
        515                 520                 525

Asp Gly Glu Thr Pro Ala Lys Phe Arg Pro Phe Asp Phe Asp Leu Ile
    530                 535                 540

Ile Ile Asp Glu Ala His Arg Ser Ile Tyr His Arg Phe Lys Arg Ile
545                 550                 555                 560

Leu Asp Tyr Phe Asp Ala Tyr Val Leu Gly Leu Thr Ala Thr Pro Lys
                565                 570                 575

Ser Glu Val His Arg Asn Thr Tyr Gln Leu Phe Asp Ile Asp Gly Lys
            580                 585                 590

Asn Pro Thr Gly Ser Tyr Thr Leu Glu Gln Ala Val Glu Asp Lys Tyr
        595                 600                 605

Leu Val Pro Pro Gln Val Ile Thr Gln Asp Ser Leu Phe Leu Arg Ser
    610                 615                 620

Gly Val Arg Tyr Glu Asp Leu Asp Val Asp Glu Gln Gln Arg Trp Asp
625                 630                 635                 640

Glu Ala Glu Trp Gly Thr Asp Glu Asp Gly Asn Pro Leu Asp Pro Pro
                645                 650                 655

Asp Gly Val Ser Ala Ala Glu Ile Asn Ser Arg Leu Tyr Asn Arg Asp
            660                 665                 670

Thr Ile Arg Lys Val Leu Lys Thr Leu Val Thr Glu Gly Ile Lys Val
        675                 680                 685

Glu Gly Gly Asp Arg Leu Gly Lys Thr Ile Ile Phe Ala Arg Thr Gln
```

-continued

```
            690                 695                 700
Lys His Ala Ser Leu Ile Lys Glu Glu Phe Asp Arg His Phe Pro Leu
705                 710                 715                 720

Tyr Ala Gly Glu Asn Ala Ser Val Ile Thr His Ser Thr Arg Tyr Ala
                725                 730                 735

Ala Ala Glu Leu Lys Arg Phe Lys Asn Pro Thr Ser Gly Leu Asn Val
                740                 745                 750

Ala Ile Ser Val Asp Met Leu Asp Thr Gly Val Asp Val Pro Glu Val
                755                 760                 765

Val Asn Leu Ile Phe Phe Lys Pro Val Tyr Ser Ser Thr Lys Phe Trp
770                 775                 780

Gln Met Met Gly Arg Gly Thr Arg Leu Arg Leu Asn Leu Phe Gly Asp
785                 790                 795                 800

Gly Ile His Lys Asp Lys Phe Arg Val Phe Asp Phe Cys Gly Asn Ala
                805                 810                 815

Arg Phe Phe Met Glu Gln Gln Pro Glu Asp Pro Gly Ile Gly Arg Gln
                820                 825                 830

Val Ser Leu Ser Glu Lys Leu Phe Leu Ser Arg Ala Ser Leu Val Ala
                835                 840                 845

Gln Leu Asp Gln Arg Asn Asp Val Pro Ala Asp Leu Arg Ile Glu Leu
850                 855                 860

Ala Ala Asp Leu His Lys Ser Val Ser Gln Ile Pro Pro Thr His Ile
865                 870                 875                 880

Gln Val Arg Pro Leu Asp Arg Pro Ile Leu Glu Tyr Tyr Gln Gln Ala
                885                 890                 895

Glu Ala Trp Lys Thr Val Thr Glu Asp Asp Val Glu Lys Leu Gly Asp
                900                 905                 910

His Ile Ala Ser Leu Pro Met Lys Thr Met Asp Glu Lys Glu Ser Ala
                915                 920                 925

Lys Arg Phe Asp Leu Leu Ile Leu Gln Leu Gln Leu Gly Leu Leu Asn
930                 935                 940

Glu Asp Thr Ser Trp Ala Lys Asn Arg Gln Arg Val Glu Lys Ile Ala
945                 950                 955                 960

Asp Glu Leu Leu Thr Val Ser Glu Asn Leu Pro Phe Val Ala Ala Ala
                965                 970                 975

Ser Lys Thr Leu Glu Ala Leu Leu Asp Ser Glu Trp Trp Glu Gly Val
                980                 985                 990

Thr Ile Pro Glu Leu Glu Lys Val Arg Arg Glu Ile Arg Asp Leu Val
                995                 1000                1005

Glu Phe Val Pro Arg His Lys Arg Gln Val Val Val Leu Asp Val
        1010                1015                1020

Glu Asp Glu Phe Gly Asp Ile Ala Glu Val Asp Leu Pro Val Glu
        1025                1030                1035

His Ala Ala Val Gly Val Asn Val Ser Arg Val Glu Glu Glu Leu
        1040                1045                1050

Arg Ala Ser Leu Asp Asp His Arg Asp Ser Leu Ala Met Gln Lys
        1055                1060                1065

Leu Arg Thr Ala Arg Pro Leu Thr Glu Ser Asp Val Glu Asp Leu
        1070                1075                1080

Glu Thr Met Val Ala Asp Thr Gly Leu Glu Gly Val Asp Glu Val
        1085                1090                1095

Arg Glu Ser Leu Gly Gly Asp Thr Ile Pro Ala Phe Val Arg Arg
        1100                1105                1110
```

Leu Val Gly Leu Asp Glu Glu Thr Met Arg Ala Glu Phe Ala Asp
    1115                1120                1125

Leu Leu Glu Gly Ser Thr Leu Thr Ala Asn Gln Ile Ser Phe Ile
    1130                1135                1140

Arg His Val Ile Lys Val Leu Val Asn Asn Gly Gly Leu Thr Met
    1145                1150                1155

Gln Glu Ala Phe Asp Glu Ser Phe Tyr Pro Tyr Gly Arg Val Ser
    1160                1165                1170

Asp Leu Phe Gln Asp Asn Gln Ala Val Val Leu Asp Leu Lys Ser
    1175                1180                1185

Arg Leu Asp Arg Ile Asn Ala Thr Ala Asp Val Ser
    1190                1195                1200

<210> SEQ ID NO 7
<211> LENGTH: 1917
<212> TYPE: DNA
<213> ORGANISM: Corynebacterium glutamicum ssp. Lactofermentum

<400> SEQUENCE: 7
atgagagtat gcccaacgct acacataacg acttgtgggt ctggatcact cttgatcaag      60
gtggctgact ctgctcccaa cggcttgtcg atctatggcc aggagaatga caacgccacc     120
tgggcactat ctcggatgaa tatgatcctt cacggcaacg agacgcacga cattcgccag     180
ggagatacgc tctctgatcc gaagtttctc aagggcgagc agttgcagac ctttgactac     240
ttcgtggcca acccaccgtt ctccgtgaag acttggaaga acggcttcga caaggaatac     300
gaccggttcg agggtttcgc tgagccgccg gagaagaacg gcgactatgc cttcttactc     360
cacatggtga agtcgctcaa gtctgatggt cggggagcgg tgattcttcc ccacggagtg     420
ctcttccgtg gtaacactga agccgcgatc cgtgaagagc tgatccggcg cggcctgatc     480
aaggcgatca tcggactgcc ggccaacctc ttctacggta cgggaattcc ggcctgcatc     540
atcgtcatcg acaagaagga cgcggcaaac cggacgggca tcttcatgat cgatgcctcc     600
aaaggctttg agaggacgg gccgaagaac cgtctgcgtc ctcgggatat gcgcaaggta     660
atcgacacct accttgctgg cgaggaaatt gagcgctacg cccgaatggt gccgctctct     720
gagatctctg atgcgaagaa caactacaac ctcaacatcc cgcgctacat cgacacctct     780
gaaccggaag acatccagga cctagaagcc catctcaagg gtggtatccc gaaccgagat     840
ctcgatgccc tgggtgaata ctgggatgct ttcccgaaac tgcgtagtga gctgttccgg     900
cctctgcggg agggatactc cgagctcacc gtagagcccg agcaggtagc caaggtgatt     960
gaggaatcgg aggacgtcaa agcttttacc tcgactgtct ccaaggctgt tgaagattgg    1020
tggagctctc accgaggcca gttggaggcg atcgactcgc agacaaggcc tcaggaattg    1080
atcgaggatc tcggtgacga cctgttggag aagtttcgcg tcgtccgct gatcagcgag     1140 tacagcgtgt acgagcagct gctgaactac tggaacgaca ccatgcatga cgacgtcaca    1200
ctgatcgtcg gtctggctg ggttgaagcc gcgcaacctc gtgaagcgcg atcaccggc     1260 tacgacaaca agaagaaggc gaagtacgag agcgccgaca tggtcttcgg aacgggggtt    1320
aaggcacagc ggtgggtaac cgacctgatc ccgccggcgc tgattatcga ccggtacttc    1380
gtcgatgaga aggctgaact ggagcggctg accgccgagc aggatcgtgc cagccaggac    1440
gtaatcgagt acatcgagga gcatggagtc gaggagggtc tgctctggga agcagtcaac    1500
gatgacggta gcatcaaggt caaggatgct cgcgaccgac tgaaggctgc caagctagaa    1560

-continued

```
gctatcgaag ccgacgagat tgccgcgctg aacacggtga tcaagctgtt tacggcagag      1620
acggcagcaa agaaggcagt caaggacgga atgttgcagc tggatacgaa ggcgatcgcc      1680
acgtatgcca agctttccaa ggaagagatc caggagttgg tggtcggcga taagtggcag      1740
gctgtcgtcg caggtcggtt cgctagtgag gtcgcccacc taactcatga tttgacgagc      1800
cgtatccggg ttcttggcga acgctacggc gagactgttg gggctatcaa cgatgaattg      1860
gtcaaactag aaagacgggt atcaggacac ctttccgcca tggggggtgaa atcatga       1917
```

<210> SEQ ID NO 8
<211> LENGTH: 638
<212> TYPE: PRT
<213> ORGANISM: Corynebacterium glutamicum ssp. Lactofermentum

<400> SEQUENCE: 8

```
Met Arg Val Cys Pro Thr Leu His Ile Thr Thr Cys Gly Ser Gly Ser
1               5                  10                  15

Leu Leu Ile Lys Val Ala Asp Ser Ala Pro Asn Gly Leu Ser Ile Tyr
            20                  25                  30

Gly Gln Glu Asn Asp Asn Ala Thr Trp Ala Leu Ser Arg Met Asn Met
        35                  40                  45

Ile Leu His Gly Asn Glu Thr His Asp Ile Arg Gln Gly Asp Thr Leu
    50                  55                  60

Ser Asp Pro Lys Phe Leu Lys Gly Glu Gln Leu Gln Thr Phe Asp Tyr
65                  70                  75                  80

Phe Val Ala Asn Pro Pro Phe Ser Val Lys Thr Trp Lys Asn Gly Phe
                85                  90                  95

Asp Lys Glu Tyr Asp Arg Phe Glu Gly Phe Ala Glu Pro Pro Glu Lys
            100                 105                 110

Asn Gly Asp Tyr Ala Phe Leu Leu His Met Val Lys Ser Leu Lys Ser
        115                 120                 125

Asp Gly Arg Gly Ala Val Ile Leu Pro His Gly Val Leu Phe Arg Gly
    130                 135                 140

Asn Thr Glu Ala Ala Ile Arg Glu Glu Leu Ile Arg Arg Gly Leu Ile
145                 150                 155                 160

Lys Ala Ile Ile Gly Leu Pro Ala Asn Leu Phe Tyr Gly Thr Gly Ile
                165                 170                 175

Pro Ala Cys Ile Ile Val Ile Asp Lys Lys Asp Ala Ala Asn Arg Thr
            180                 185                 190

Gly Ile Phe Met Ile Asp Ala Ser Lys Gly Phe Glu Lys Asp Gly Pro
        195                 200                 205

Lys Asn Arg Leu Arg Pro Arg Asp Met Arg Lys Val Ile Asp Thr Tyr
    210                 215                 220

Leu Ala Gly Glu Glu Ile Glu Arg Tyr Ala Arg Met Val Pro Leu Ser
225                 230                 235                 240

Glu Ile Ser Asp Ala Lys Asn Asn Tyr Asn Leu Asn Ile Pro Arg Tyr
                245                 250                 255

Ile Asp Thr Ser Glu Pro Glu Asp Ile Gln Asp Leu Glu Ala His Leu
            260                 265                 270

Lys Gly Gly Ile Pro Asn Arg Asp Leu Asp Ala Leu Gly Glu Tyr Trp
        275                 280                 285

Asp Ala Phe Pro Lys Leu Arg Ser Glu Leu Phe Arg Pro Leu Arg Glu
    290                 295                 300

Gly Tyr Ser Glu Leu Thr Val Glu Pro Glu Gln Val Ala Lys Val Ile
305                 310                 315                 320
```

-continued

```
Glu Glu Ser Glu Asp Val Lys Ala Phe Thr Ser Thr Val Ser Lys Ala
            325                 330                 335

Val Glu Asp Trp Trp Ser Ser His Arg Gly Gln Leu Glu Ala Ile Asp
            340                 345                 350

Ser Gln Thr Arg Pro Gln Glu Leu Ile Glu Asp Leu Gly Asp Asp Leu
            355                 360                 365

Leu Glu Lys Phe Arg Gly Arg Pro Leu Ile Ser Glu Tyr Ser Val Tyr
    370                 375                 380

Glu Gln Leu Leu Asn Tyr Trp Asn Asp Thr Met His Asp Asp Val Thr
385                 390                 395                 400

Leu Ile Val Gly Ser Gly Trp Val Glu Ala Gln Pro Arg Glu Ala
            405                 410                 415

Arg Ile Thr Gly Tyr Asp Asn Lys Lys Ala Lys Tyr Glu Ser Ala
            420                 425                 430

Asp Met Val Phe Gly Thr Gly Val Lys Ala Gln Arg Trp Val Thr Asp
            435                 440                 445

Leu Ile Pro Pro Ala Leu Ile Ile Asp Arg Tyr Phe Val Asp Glu Lys
    450                 455                 460

Ala Glu Leu Glu Arg Leu Thr Ala Glu Gln Asp Arg Ala Ser Gln Asp
465                 470                 475                 480

Val Ile Glu Tyr Ile Glu Glu His Gly Val Glu Glu Gly Leu Leu Trp
            485                 490                 495

Glu Ala Val Asn Asp Asp Gly Ser Ile Lys Val Lys Asp Ala Arg Asp
            500                 505                 510

Arg Leu Lys Ala Ala Lys Leu Glu Ala Ile Glu Ala Asp Glu Ile Ala
            515                 520                 525

Ala Leu Asn Thr Val Ile Lys Leu Phe Thr Ala Glu Thr Ala Ala Lys
            530                 535                 540

Lys Ala Val Lys Asp Gly Met Leu Gln Leu Asp Thr Lys Ala Ile Ala
545                 550                 555                 560

Thr Tyr Ala Lys Leu Ser Lys Glu Glu Ile Gln Glu Leu Val Val Gly
            565                 570                 575

Asp Lys Trp Gln Ala Val Val Ala Gly Arg Phe Ala Ser Glu Val Ala
            580                 585                 590

His Leu Thr His Asp Leu Thr Ser Arg Ile Arg Val Leu Gly Glu Arg
            595                 600                 605

Tyr Gly Glu Thr Val Gly Ala Ile Asn Asp Glu Leu Val Lys Leu Glu
    610                 615                 620

Arg Arg Val Ser Gly His Leu Ser Ala Met Gly Val Lys Ser
625                 630                 635
```

<210> SEQ ID NO 9
<211> LENGTH: 1236
<212> TYPE: DNA
<213> ORGANISM: Corynebacterium glutamicum ssp. Lactofermentum

<400> SEQUENCE: 9

| | | | | |
|---|---|---|---|---|
| atgactgaat ggactcaacg aaaagtctcg gatctcatcg atgggttaag agctggagtc | 60 |
| agcgtcagat cttccccggg agttaacggt ggaccagcgg ttctaaaaac ttcggctatc | 120 |
| aaatcgggcc gatttgatcc cagcgaagtc aagacgattt tgaaagcgga cctacaaagg | 180 |
| gcaaagtgtc ctgtggcagc cgacagtttg atcatcagtc ggatgaatac acctgctctt | 240 |
| gttggggatg tcggttacgt cgatgaagac cgcgcagatc tctatcttcc agaccggctt | 300 |

```
tggctagcgc agaaaaagcg caactcagat actgatatgc gatggctcac gtaccacttc      360
tcttctggga caggcgctcg tgcacttcga gacctggcta ctggcaccag cggaagcatg      420
aagaatatcc ccaaaaataa agtcttaaac ctggtgatcc tcacgccgag cgctctcgag      480
cagcaagcaa ttgctgatgc gattaccaat actgatgacc tcatcgaatc tctcgagcgc      540
ctcatctcca agaagcaggc aataaagcag ggcatgatgc aggagctgct taccggtcgc      600
actcgcctgc cagggtttac tgcagaatgg aaggaatcaa ggctaggtag tttcggcacg      660
ttccttaaag ggagagggat taaacgcgac gaaattcagt cacgtggtgt gccttgcatt      720
aggtacggag agctatatac cacgtttgaa actatacag aaaaaacggc ttccttcgtc       780
tcggatgata ttgcagctac agcgcttccg attcgctatg cgacattct ctttgcaggg       840 tcaggcgaga caaaagcgga aattggaaca aacgttgctt acctcggaaa agtgcaggca      900
gttgccgggg gtgacatcat cgttttcgg ggaatttctc ataatccagt ttttctatcc       960
tctttgctca actctcccgc aatcgccgcc cagaaggcaa gggctggaca aggggatgcg     1020
attgttcata ttcattccag ctccctagcg gagatagtgg ttaatgttcc gccaatcgaa     1080
gagcaggaag ctattgcaca gatcctgcag gatgccgaca ggaaatcgc tgcgcttgat      1140 cgtcgtctcg aaaccgctcg caatatcaag accggcatga tgcaggagct ccttaccggt     1200
cgaacccgcc tgcccgtcga ggaggtctca tcatga                              1236

<210> SEQ ID NO 10
<211> LENGTH: 411
<212> TYPE: PRT
<213> ORGANISM: Corynebacterium glutamicum ssp. Lactofermentum

<400> SEQUENCE: 10

Met Thr Glu Trp Thr Gln Arg Lys Val Ser Asp Leu Ile Asp Gly Leu
1               5                   10                  15

Arg Ala Gly Val Ser Val Arg Ser Pro Gly Val Asn Gly Gly Pro
            20                  25                  30

Ala Val Leu Lys Thr Ser Ala Ile Lys Ser Gly Arg Phe Asp Pro Ser
        35                  40                  45

Glu Val Lys Thr Ile Leu Lys Ala Asp Leu Gln Arg Ala Lys Cys Pro
    50                  55                  60

Val Ala Ala Asp Ser Leu Ile Ile Ser Arg Met Asn Thr Pro Ala Leu
65                  70                  75                  80

Val Gly Asp Val Gly Tyr Val Asp Glu Asp Arg Ala Asp Leu Tyr Leu
                85                  90                  95

Pro Asp Arg Leu Trp Leu Ala Gln Lys Lys Arg Asn Ser Asp Thr Asp
            100                 105                 110

Met Arg Trp Leu Thr Tyr His Phe Ser Ser Gly Thr Gly Ala Arg Ala
        115                 120                 125

Leu Arg Asp Leu Ala Thr Gly Thr Ser Gly Ser Met Lys Asn Ile Pro
    130                 135                 140

Lys Asn Lys Val Leu Asn Leu Val Ile Leu Thr Pro Ser Ala Leu Glu
145                 150                 155                 160

Gln Gln Ala Ile Ala Asp Ala Ile Thr Asn Thr Asp Asp Leu Ile Glu
                165                 170                 175

Ser Leu Glu Arg Leu Ile Ser Lys Lys Gln Ala Ile Lys Gln Gly Met
            180                 185                 190

Met Gln Glu Leu Leu Thr Gly Arg Thr Arg Leu Pro Gly Phe Thr Ala
        195                 200                 205
```

-continued

```
Glu Trp Lys Glu Ser Arg Leu Gly Ser Phe Gly Thr Phe Leu Lys Gly
    210                 215                 220

Arg Gly Ile Lys Arg Asp Glu Ile Gln Ser Arg Gly Val Pro Cys Ile
225                 230                 235                 240

Arg Tyr Gly Glu Leu Tyr Thr Thr Phe Glu Asn Tyr Thr Glu Lys Thr
                245                 250                 255

Ala Ser Phe Val Ser Asp Asp Ile Ala Ala Thr Ala Leu Pro Ile Arg
            260                 265                 270

Tyr Gly Asp Ile Leu Phe Ala Gly Ser Gly Glu Thr Lys Ala Glu Ile
        275                 280                 285

Gly Thr Asn Val Ala Tyr Leu Gly Lys Val Gln Ala Val Ala Gly Gly
    290                 295                 300

Asp Ile Ile Val Phe Arg Gly Ile Ser His Asn Pro Val Phe Leu Ser
305                 310                 315                 320

Ser Leu Leu Asn Ser Pro Ala Ile Ala Ala Gln Lys Ala Arg Ala Gly
                325                 330                 335

Gln Gly Asp Ala Ile Val His Ile His Ser Ser Leu Ala Glu Ile
            340                 345                 350

Val Val Asn Val Pro Pro Ile Glu Glu Gln Ala Ile Ala Gln Ile
        355                 360                 365

Leu Gln Asp Ala Asp Lys Glu Ile Ala Ala Leu Asp Arg Arg Leu Glu
    370                 375                 380

Thr Ala Arg Asn Ile Lys Thr Gly Met Met Gln Glu Leu Leu Thr Gly
385                 390                 395                 400

Arg Thr Arg Leu Pro Val Glu Glu Val Ser Ser
                405                 410
```

<210> SEQ ID NO 11
<211> LENGTH: 3087
<212> TYPE: DNA
<213> ORGANISM: Corynebacterium glutamicum ssp. Lactofermentum

<400> SEQUENCE: 11

```
atgagttcca ttggacagcg tgagcgtctc acgcaagatc gggtagtcgg catactctca      60
agccagctga actatgagta tgccggcgac tggaaagatc gcggcaattc caacgtcgag     120
gaggagctgc ttcgccagaa cctgcttgct cgtggataca gcgaggatct cgttcgtcgc     180
gctattcagc agtttgtcac cgccgcttct ctgccagcgg gtggatcact ttacgacgcg     240
aaccgcagag tgtatggcct gctccgctac ggcgtaaagg tcaagcgcag cgtttcggag     300
aacttcgaga cggtgtggct tatcgactgg aaggacccgg aggctaatca ctttgtggtg     360
gctgaagagg tctctatcaa gggtaagaac accaaacgtc ctgacgtcgt gctctacgtc     420
aatggcatcg ctctcggggt tatagagctc aagcgctcta aggtcagcgt tggtgatggt     480
atccgtcagc atctcggcaa ccagaaggcg gacttcgttc gtccttctct tcaccaccgtc    540
cagctactgt tcgctggtaa tgacgtcgag gggcttcgct atggcgtgat cgagacgccg     600
gagaagtact ggctggagtg gacagagcca agcgaggttg agaaacccct tgaccgtggc     660
ctgcttcaga tggcgaacaa caacgcttc ctcgaactca tccatgacta cattgtcttt      720
gattcgggcg tgaagaaaac cgcccgacac aaccagtact tcggcgtcaa ggccgcccag     780
gaacgcatcg ctcgtcgaga aggcgggatt atttggcaca cccaaggttc aggcaagagc     840
ttgacgatgg tatggctggc caaatggatt cgggaaaacc agcgcgaggc gcgcgtcctg     900
gtgatcactg accgcaccga acttgatgag cagatcgaga aggtctttgc cggcgtcgac     960
```

```
gagaccatcg atcgatcgac gtctggatcc ggcatgatcg gtatgctcaa ccggaaccaa    1020
ccatggttga tgtgctcact cgttcataag ttccgaggtg atgacgaaaa ggatcagggc    1080
gacacggaag acttcgtgcg tcagctcaag aagcccatgc ttgatggttt cagccctaag    1140
ggcaatctct tcgtcttcgt cgatgaggcc accgcaccc agagcggcaa gctccacagc    1200
gcgatgaagg agctgctacc gaacgcgatg ttcatcggct ttaccggcac gcctcttctg    1260
aagaaagata aggcctctag tattgaggcc ttcggatcgt acattcacac ttacaagttt    1320
gatgaagcag ttaaagacaa ggtagtgctg gatctacgct acgaagcccg tgacatcgag    1380
caaaaactta tgagcccaga acgggttgat gagtggttca agatccacac taaaggcatg    1440
accgatctca gtaaacaccg gctcaagcag cgctgggcca cgatcaaggc agttgaatcg    1500
gcagagccac gggccaggca gatcgcagct gacatactaa tggatatggc acgaatgcct    1560
cgcctgatgg atggtcgagg caacgccatg ctggtctgct cgagtgttta ccaagcctgc    1620
aaattctacg agatcttcag tcgtagcgag cttgccggca agatagcgat aatcaccagt    1680
tatgagccga atgcgtcgca gatctccaag gaagattctg gggccggcaa gaatgaagag    1740
atcgtgaagt atgagacgta tcgtcgcatg ctggctgact acttccagac caacgccgat    1800
gatgcggcca agcggatcga ggagtttgag aagagcgtca agaaacgtt catcaagcac    1860 ccgggccaga tgcgtcttct catcgtggtc gataagctgc tgaccggctt cgatgccccg    1920
agcgctacct atctctatat cgataagaac atgcaggatc atggtctgtt ccaggccatc    1980
tgccgtgtta accggcttga tggtgacgat aaggaatacg gttacatcgt ggattatcgt    2040
gatctgttca gtcgctcga gactgcagtg tctgactaca cctcagaagc cttcggtgac    2100
tacgaccaag acgatatcga cgggctactt aaagaccgta ttgaacagga gcgccaggat    2160
ctcgatgacg ctctcgagaa ggtacgcgcc ctatgcgagc cggtcgcccc acctaagggc    2220
acgttgcagt accagcacta tttctgtgcg attgaaagtg gtaacgctga gcagctcaaa    2280
gccaatgaac caaagcgcgt agatctctac aagggtgtgg cgagcttggt gagggcttac    2340
gccaacctag ccaatcgtat gagtgaggcc ggttactccg aaaccgatgc tgaattcatc    2400
aagcgccagg tcaagcactt cgtcgatgtc cgcgacgagg taaagcttgg tgctggcgag    2460
aatatggatc ttaaacagtt cgaggcgggc atgcgttccc tgctggatac ttatatccag    2520
gcagacgctt cccgaaacct cgcgaccttt gaccagggc tcgtgcaact catcgtcgaa    2580
catggagttg gggctttgga gaaacttccg gagaacatcc gaaagacccc ggaggctgcg    2640
gctgaaacca tcgtcaataa cgtccgtaag acaatcgttg acgaacaggc catgaacccg    2700
aagtattacg agtctatgtc tactctgctc gatgctctga ttgagcagcg tcgtgaggct    2760
gtgatcgact acgaggagta tctgcttaag ctggttgagt tcacccagcg tctcgctaag    2820
ggcgaatctg ataggaagtt ccctgactgg gccaagacgc cagctcgccg ggctctgatc    2880
gacttcgcgt ggccccaggg cattgaggtt gatgtggaac gtgtatatag caccatccaa    2940
cgcaataaag aacatggctg gtctggagat aagaccaagc aaaagtctct gatgcgtact    3000
cttgcactca acttccctgg gctcctagat aaaacgcaga tggaaagtct gcttgatcaa    3060
ctgaaaaagc atgatgaatt ccgctag                                       3087
```

<210> SEQ ID NO 12
<211> LENGTH: 1028
<212> TYPE: PRT
<213> ORGANISM: Corynebacterium glutamicum ssp. Lactofermentum

<400> SEQUENCE: 12

```
Met Ser Ser Ile Gly Gln Arg Glu Arg Leu Thr Gln Asp Arg Val Val
1               5                   10                  15

Gly Ile Leu Ser Ser Gln Leu Asn Tyr Glu Tyr Ala Gly Asp Trp Lys
                20                  25                  30

Asp Arg Gly Asn Ser Asn Val Glu Glu Leu Leu Arg Gln Asn Leu
            35                  40                  45

Leu Ala Arg Gly Tyr Ser Glu Asp Leu Val Arg Ala Ile Gln Gln
50                  55                  60

Phe Val Thr Ala Ala Ser Leu Pro Ala Gly Gly Ser Leu Tyr Asp Ala
65                  70                  75                  80

Asn Arg Arg Val Tyr Gly Leu Leu Arg Tyr Gly Val Lys Val Lys Arg
                85                  90                  95

Ser Val Ser Glu Asn Phe Glu Thr Val Trp Leu Ile Asp Trp Lys Asp
                100                 105                 110

Pro Glu Ala Asn His Phe Val Ala Glu Glu Val Ser Ile Lys Gly
            115                 120                 125

Lys Asn Thr Lys Arg Pro Asp Val Val Leu Tyr Val Asn Gly Ile Ala
    130                 135                 140

Leu Gly Val Ile Glu Leu Lys Arg Ser Lys Val Ser Val Gly Asp Gly
145                 150                 155                 160

Ile Arg Gln His Leu Gly Asn Gln Lys Ala Asp Phe Val Arg Pro Phe
                165                 170                 175

Phe Thr Thr Val Gln Leu Leu Phe Ala Gly Asn Asp Val Glu Gly Leu
            180                 185                 190

Arg Tyr Gly Val Ile Glu Thr Pro Glu Lys Tyr Trp Leu Glu Trp Thr
                195                 200                 205

Glu Pro Ser Glu Val Glu Lys Pro Leu Asp Arg Gly Leu Leu Gln Met
    210                 215                 220

Ala Asn Lys Gln Arg Phe Leu Glu Leu Ile His Asp Tyr Ile Val Phe
225                 230                 235                 240

Asp Ser Gly Val Lys Lys Thr Ala Arg His Asn Gln Tyr Phe Gly Val
                245                 250                 255

Lys Ala Ala Gln Glu Arg Ile Ala Arg Arg Glu Gly Gly Ile Ile Trp
                260                 265                 270

His Thr Gln Gly Ser Gly Lys Ser Leu Thr Met Val Trp Leu Ala Lys
            275                 280                 285

Trp Ile Arg Glu Asn Gln Arg Glu Ala Arg Val Leu Val Ile Thr Asp
    290                 295                 300

Arg Thr Glu Leu Asp Glu Gln Ile Glu Lys Val Phe Ala Gly Val Asp
305                 310                 315                 320

Glu Thr Ile Asp Arg Ser Thr Ser Gly Ser Gly Met Ile Gly Met Leu
                325                 330                 335

Asn Arg Asn Gln Pro Trp Leu Met Cys Ser Leu Val His Lys Phe Arg
                340                 345                 350

Gly Asp Asp Glu Lys Asp Gln Gly Asp Thr Glu Asp Phe Val Arg Gln
            355                 360                 365

Leu Lys Lys Pro Met Leu Asp Gly Phe Ser Pro Lys Gly Asn Leu Phe
370                 375                 380

Val Phe Val Asp Glu Ala His Arg Thr Gln Ser Gly Lys Leu His Ser
385                 390                 395                 400

Ala Met Lys Glu Leu Leu Pro Asn Ala Met Phe Ile Gly Phe Thr Gly
                405                 410                 415
```

```
Thr Pro Leu Leu Lys Lys Asp Lys Ala Ser Ser Ile Glu Ala Phe Gly
            420                 425                 430

Ser Tyr Ile His Thr Tyr Lys Phe Asp Glu Ala Val Lys Asp Lys Val
        435                 440                 445

Val Leu Asp Leu Arg Tyr Glu Ala Arg Asp Ile Glu Gln Lys Leu Met
    450                 455                 460

Ser Pro Glu Arg Val Asp Glu Trp Phe Lys Ile His Thr Lys Gly Met
465                 470                 475                 480

Thr Asp Leu Ser Lys His Arg Leu Lys Gln Arg Trp Ala Thr Ile Lys
                485                 490                 495

Ala Val Glu Ser Ala Glu Pro Arg Ala Arg Gln Ile Ala Ala Asp Ile
            500                 505                 510

Leu Met Asp Met Ala Arg Met Pro Arg Leu Met Asp Gly Arg Gly Asn
        515                 520                 525

Ala Met Leu Val Cys Ser Ser Val Tyr Gln Ala Cys Lys Phe Tyr Glu
    530                 535                 540

Ile Phe Ser Arg Ser Glu Leu Ala Gly Lys Ile Ala Ile Ile Thr Ser
545                 550                 555                 560

Tyr Glu Pro Asn Ala Ser Gln Ile Ser Lys Glu Asp Ser Gly Ala Gly
                565                 570                 575

Lys Asn Glu Glu Ile Val Lys Tyr Glu Thr Tyr Arg Arg Met Leu Ala
            580                 585                 590

Asp Tyr Phe Gln Thr Asn Ala Asp Ala Ala Lys Arg Ile Glu Glu
        595                 600                 605

Phe Glu Lys Ser Val Lys Glu Thr Phe Ile Lys His Pro Gly Gln Met
    610                 615                 620

Arg Leu Leu Ile Val Val Asp Lys Leu Leu Thr Gly Phe Asp Ala Pro
625                 630                 635                 640

Ser Ala Thr Tyr Leu Tyr Ile Asp Lys Asn Met Gln Asp His Gly Leu
                645                 650                 655

Phe Gln Ala Ile Cys Arg Val Asn Arg Leu Asp Gly Asp Asp Lys Glu
            660                 665                 670

Tyr Gly Tyr Ile Val Asp Tyr Arg Asp Leu Phe Lys Ser Leu Glu Thr
        675                 680                 685

Ala Val Ser Asp Tyr Thr Ser Glu Ala Phe Gly Asp Tyr Asp Gln Asp
    690                 695                 700

Asp Ile Asp Gly Leu Leu Lys Asp Arg Ile Glu Gln Glu Arg Gln Asp
705                 710                 715                 720

Leu Asp Asp Ala Leu Glu Lys Val Arg Ala Leu Cys Glu Pro Val Ala
                725                 730                 735

Pro Pro Lys Gly Thr Leu Gln Tyr Gln His Tyr Phe Cys Ala Ile Glu
            740                 745                 750

Ser Gly Asn Ala Glu Gln Leu Lys Ala Asn Glu Pro Lys Arg Val Asp
        755                 760                 765

Leu Tyr Lys Gly Val Ala Ser Leu Val Arg Ala Tyr Ala Asn Leu Ala
    770                 775                 780

Asn Arg Met Ser Glu Ala Gly Tyr Ser Glu Thr Asp Ala Glu Phe Ile
785                 790                 795                 800

Lys Arg Gln Val Lys His Phe Val Asp Val Arg Asp Glu Val Lys Leu
                805                 810                 815

Gly Ala Gly Glu Asn Met Asp Leu Lys Gln Phe Glu Ala Gly Met Arg
            820                 825                 830

Ser Leu Leu Asp Thr Tyr Ile Gln Ala Asp Ala Ser Arg Asn Leu Ala
```

```
                835            840            845
Thr Phe Asp Gln Gly Leu Val Gln Leu Ile Val Glu His Gly Val Gly
    850                 855                 860

Ala Leu Glu Lys Leu Pro Glu Asn Ile Arg Lys Thr Pro Glu Ala Ala
865                 870                 875                 880

Ala Glu Thr Ile Val Asn Asn Val Arg Lys Thr Ile Val Asp Glu Gln
                885                 890                 895

Ala Met Asn Pro Lys Tyr Tyr Glu Ser Met Ser Thr Leu Leu Asp Ala
            900                 905                 910

Leu Ile Glu Gln Arg Arg Glu Ala Val Ile Asp Tyr Glu Glu Tyr Leu
        915                 920                 925

Leu Lys Leu Val Glu Phe Thr Gln Arg Leu Ala Lys Gly Glu Ser Asp
    930                 935                 940

Arg Lys Phe Pro Asp Trp Ala Lys Thr Pro Ala Arg Arg Ala Leu Ile
945                 950                 955                 960

Asp Phe Ala Trp Pro Gln Gly Ile Glu Val Asp Val Glu Arg Val Tyr
                965                 970                 975

Ser Thr Ile Gln Arg Asn Lys Glu His Gly Trp Ser Gly Asp Lys Thr
            980                 985                 990

Lys Gln Lys Ser Leu Met Arg Thr  Leu Ala Leu Asn Phe  Pro Gly Leu
        995                 1000                1005

Leu Asp  Lys Thr Gln Met Glu  Ser Leu Leu Asp Gln  Leu Lys Lys
    1010                1015                1020

His Asp  Glu Phe Arg
    1025
```

<210> SEQ ID NO 13
<211> LENGTH: 2034
<212> TYPE: DNA
<213> ORGANISM: Corynebacterium glutamicum ssp. Lactofermentum

<400> SEQUENCE: 13

```
atgaaattcc tcgtagatct ggaaaactta cttaaaaagg atgagcgttt catctcatca      60
gatggtcagc tgttaaagcc tcttatacgg gatgcggcag acagctcga tccattgcta     120
atccgcgctt tgttggattc ctctgatctc tcagatcatt ttttcaaacg agtcgatgac    180
atcgtggttt tcgatcgtga aagttcatg tgggttgtta attcaaagga atttttacct    240
gacagctaca ccaagtaccg aaatagaatc ggtcttttcta cagatgatcg cagtcttttg    300
gcttcatcca gtgaaattac actcatctgg ccgtacaagg attgcgttct cgaaggtggt    360
caggagaaag aggacgagga acgcgatgaa attttttaca atgagactct tgccccagat    420
gaagtcggtc gtcttctagc tccgaaggct tttcgaaatg ctcggagata tgtgaatgga    480
gattctgaac cgatagacca gttctccca gaggacaatc taattattcg gggcaataat    540
ctcctcgctt tgagttctct tttggaaaga tatgaggggc aggtcaaatg tatttatatc    600
gatccgccat ataatacggg ctccgatagc ttccgctata atgatcgatt taatcattct    660
agctggttaa ccttcatgaa aaataggctc gacctagcca agcggctcct gagccgagac    720
ggtttcatcc ttgtgcaatg cgatgataat gagcaggcat atttgaaagt cctgatggac    780
tcagttttcg gtaacaaaa tttcattaac gttatatcgg tgcgtacgaa ggtcggagga    840
gtcactggct cttctgctgg aaaaagcttg aaagatgaac ttgagtacat caatctgttt    900
gccaaggatc gatcttctga gtctgcaaat ttgacaccga cctatgtaga tactgattta    960
gaagaataca ttcagtccta caaagactca ggaaagagtt ggaaatatac gtcggtccta   1020
```

-continued

```
acaaagttgg aaggtcgcgt tctgcttgaa gaggatgaag ttcgaggtga gcggctttac    1080
ggctattcac acgtagaatc aaaatctgtt aaagctttcg ctaagcaaga gggaataact    1140
gaaggtgaag tctacgccaa gtttgcagag cgaattttcc gaactacgaa tgctcagagt    1200
tcggtgcgag ctcgcgtgat gggtcaggct tctcaatacg attttgaaat gatcggcttg    1260
gaatatactc cttcgaaggg caagaacgct agtaagaaaa tagaggttct ttataagggc    1320
aagcagcaaa atatgatgat gttcttatcc gatgctgtga gcatgcgaga tgggaaatac    1380
gtttatcaag accgtgtagg aactctctgg tctgatatcc agtacaacaa cctggcaaaa    1440
gaaggtgaag tttccttcct gaacggcaag aaacccgaag ctttaattca acgtgttctg    1500
gatctaacaa ccgaacccgg cgatctcgtt cttgatttt tcttgggttc tggcagtaca    1560
gcggcggtag cccacaaaat ggggcggaga tacctgggag tcgagcagct ggattacatc    1620
acctcggtca cggttcctcg tttggaaaag gtacttgctg gggagcagtc aggcatctcc    1680
cgagcccaaa actggcaagg aggtggttct ttcgtgtatg tcgaacttgc tgaacaaggt    1740
gaaaagctca tggtagaact ccaagaggct gggagcgcta atgaagtcca gagagtatta    1800
cagaaagcaa ctgcccaagg cctgttgaga acttcagtgc ttccaagtga ccttaagtcg    1860
aatgagaatg aattcgatga actatctttg attgatcaaa aaaacgtggt tgcagagctt    1920
attgataaga accgcctcta tgtcaacgcc agtggtatag aagatgatga ccttgagctt    1980
gatcttgccg atattgcgtt tactaagagc ttctacgagg taggtaccaa gtga          2034
```

<210> SEQ ID NO 14
<211> LENGTH: 677
<212> TYPE: PRT
<213> ORGANISM: Corynebacterium glutamicum ssp. Lactofermentum

<400> SEQUENCE: 14

```
Met Lys Phe Leu Val Asp Leu Glu Asn Leu Leu Lys Lys Asp Glu Arg
1               5                   10                  15

Phe Ile Ser Ser Asp Gly Gln Leu Leu Lys Pro Leu Ile Arg Asp Ala
                20                  25                  30

Ala Gly Gln Leu Asp Pro Leu Leu Ile Arg Ala Leu Leu Asp Ser Ser
            35                  40                  45

Asp Leu Ser Asp His Phe Phe Lys Arg Val Asp Ile Val Val Phe
        50                  55                  60

Asp Arg Glu Lys Phe Met Trp Val Val Asn Ser Lys Glu Phe Leu Pro
65                  70                  75                  80

Asp Ser Tyr Thr Lys Tyr Arg Asn Arg Ile Gly Leu Ser Thr Asp Asp
                85                  90                  95

Arg Ser Leu Leu Ala Ser Ser Ser Glu Ile Thr Leu Ile Trp Pro Tyr
            100                 105                 110

Lys Asp Cys Val Leu Glu Gly Gly Gln Glu Lys Glu Asp Glu Glu Arg
        115                 120                 125

Asp Glu Ile Phe Tyr Asn Glu Thr Leu Ala Pro Asp Glu Val Gly Arg
    130                 135                 140

Leu Leu Ala Pro Lys Ala Phe Arg Asn Ala Arg Arg Tyr Val Asn Gly
145                 150                 155                 160

Asp Ser Glu Pro Ile Asp Gln Phe Ser Pro Glu Asp Asn Leu Ile Ile
                165                 170                 175

Arg Gly Asn Asn Leu Leu Ala Leu Ser Ser Leu Leu Glu Arg Tyr Glu
            180                 185                 190
```

```
Gly Gln Val Lys Cys Ile Tyr Ile Asp Pro Pro Tyr Asn Thr Gly Ser
            195                 200                 205

Asp Ser Phe Arg Tyr Asn Asp Arg Phe Asn His Ser Ser Trp Leu Thr
            210                 215                 220

Phe Met Lys Asn Arg Leu Asp Leu Ala Lys Arg Leu Leu Ser Arg Asp
225                 230                 235                 240

Gly Phe Ile Leu Val Gln Cys Asp Asp Asn Glu Gln Ala Tyr Leu Lys
            245                 250                 255

Val Leu Met Asp Ser Val Phe Gly Glu Gln Asn Phe Ile Asn Val Ile
            260                 265                 270

Ser Val Arg Thr Lys Val Gly Val Thr Gly Ser Ser Ala Gly Lys
            275                 280                 285

Ser Leu Lys Asp Glu Leu Glu Tyr Ile Asn Leu Phe Ala Lys Asp Arg
            290                 295                 300

Ser Ser Glu Ser Ala Asn Leu Thr Pro Thr Tyr Val Asp Thr Asp Leu
305                 310                 315                 320

Glu Glu Tyr Ile Gln Ser Tyr Lys Asp Ser Gly Lys Ser Trp Lys Tyr
            325                 330                 335

Thr Ser Val Leu Thr Lys Leu Glu Gly Arg Val Leu Leu Glu Glu Asp
            340                 345                 350

Glu Val Arg Gly Glu Arg Leu Tyr Gly Tyr Ser His Val Glu Ser Lys
            355                 360                 365

Ser Val Lys Ala Phe Ala Lys Gln Glu Gly Ile Thr Glu Gly Glu Val
            370                 375                 380

Tyr Ala Lys Phe Ala Glu Arg Ile Phe Arg Thr Thr Asn Ala Gln Ser
385                 390                 395                 400

Ser Val Arg Ala Arg Val Met Gly Gln Ala Ser Gln Tyr Asp Phe Glu
            405                 410                 415

Met Ile Gly Leu Glu Tyr Thr Pro Ser Lys Gly Lys Asn Ala Ser Lys
            420                 425                 430

Lys Ile Glu Val Leu Tyr Lys Gly Lys Gln Gln Asn Met Met Met Phe
            435                 440                 445

Leu Ser Asp Ala Val Ser Met Arg Asp Gly Lys Tyr Val Tyr Gln Asp
            450                 455                 460

Arg Val Gly Thr Leu Trp Ser Asp Ile Gln Tyr Asn Asn Leu Ala Lys
465                 470                 475                 480

Glu Gly Glu Val Ser Phe Leu Asn Gly Lys Lys Pro Glu Ala Leu Ile
            485                 490                 495

Gln Arg Val Leu Asp Leu Thr Thr Glu Pro Gly Asp Leu Val Leu Asp
            500                 505                 510

Phe Phe Leu Gly Ser Gly Ser Thr Ala Ala Val Ala His Lys Met Gly
            515                 520                 525

Arg Arg Tyr Leu Gly Val Glu Gln Leu Asp Tyr Ile Thr Ser Val Thr
            530                 535                 540

Val Pro Arg Leu Glu Lys Val Leu Ala Gly Glu Gln Ser Gly Ile Ser
545                 550                 555                 560

Arg Ala Gln Asn Trp Gln Gly Gly Gly Ser Phe Val Tyr Val Glu Leu
            565                 570                 575

Ala Glu Gln Gly Glu Lys Leu Met Val Glu Leu Gln Glu Ala Gly Ser
            580                 585                 590

Ala Asn Glu Val Gln Arg Val Leu Gln Lys Ala Thr Ala Gln Gly Leu
            595                 600                 605

Leu Arg Thr Ser Val Leu Pro Ser Asp Leu Lys Ser Asn Glu Asn Glu
```

```
                    610                 615                 620
Phe Asp Glu Leu Ser Leu Ile Asp Gln Lys Asn Val Val Ala Glu Leu
625                 630                 635                 640

Ile Asp Lys Asn Arg Leu Tyr Val Asn Ala Ser Gly Ile Glu Asp Asp
                645                 650                 655

Asp Leu Glu Leu Asp Leu Ala Asp Ile Ala Phe Thr Lys Ser Phe Tyr
            660                 665                 670

Glu Val Gly Thr Lys
            675

<210> SEQ ID NO 15
<211> LENGTH: 2646
<212> TYPE: DNA
<213> ORGANISM: Corynebacterium glutamicum ssp. Lactofermentum

<400> SEQUENCE: 15
gtgagttcct cagcaacaga cctggatctt ttcctttttcc aagagcttga cctatttcta    60
gatcgatttg gaaaacgcaa agaggtccct acacacataa gccgaaatct agctccgcaa   120
atatcattgc gcgagtacca gaaacatgct tttactaata ctctcgaata tttggaaaac   180
gaaagttttt caaagaaccg acagactcat ctgctttatc acatggcaac aggttctggt   240
aaaaccgtta tgatggcagg tctcatcctg cactatttct cgctgggtta ccgcaatttt   300
cttttctttg taaaccagac gaacatcatc gagaaaacta atccaacttt tctcaagccg   360
gactcgtcaa agtaccttttt tgcagaccat attgagatca atggtgcccc tgtaagaatc   420
aatgaagtag aaacctttttc tgcttctgat ccgaatgccg taaacatctg ctttacgact   480
acgcataagc tgcacgggga tttcttcttt gctacagaga attctcttag tcaagatgac   540
tttgaagaag cgccggtagt gatgatttct gatgaatctc accatgtgaa tactcgtaca   600
aagaaagcta ctaaaagcga aaaagacgaa gatagttcgt gggaatatac ggtctcgagt   660
gcatttgcaa gcaatcgtga caacgttcta cttgagttta ctgcgacggt agatctgcgg   720
gatagaaata tcctcgctaa atataggaac aagattgtct ttgattaccc gttggctaaa   780
ttccgtgact cgggttttac aaaggacttt cagaactttc agtcatcgct tgacccgtgg   840
gggcgcacgc tgcaggcgtt gatcctatct gaatatcgtc gttcgctttt cgccgatggg   900
ggtgtctatg caaaaccggt cgttcttttg aagtcacaag caattaaaga atcaaatgag   960
ttttatacag agttttttcca acgcctgaga cagcttcag aggatagaat ccgcagtttc  1020
gcgacagagg aggtgatagg ccaggctgtt gaatactttg ccgctaaaga cccgacccta  1080
cgatcactcc gcattagcct tcaacagtct tttgctgagg agaacgcaat cattatgaat  1140
ggttctaccg acaacacggt agagaaacag cttgccgtca actctcttga ggaccattca  1200
aacccgtatc gaattatctt tactgtcgat atgctcaacg agggatggga tgttcttaac  1260
ctttatgaca ttgtgcgtct atacgaaacg aggcagggcg aaaaggcgg aaagccaggt  1320
tcttacacga tccaggaagc acagttgatt gggcgaggag ctcgttactt cccctttatt  1380
ctcaacaaag aacttgacat tcgtgagccc gaagaggctc gagtgcgtaa gtatgacgct  1440
gacctcgaaa acccgcatcg cttactagaa acattgcttt accactcgaa gcaggactct  1500
aagtatattg ctgaactacg tcttgcactc agggaaactg gtcttttacc taatgatatt  1560
actgaagtta cctacgaggt gaagcctgat ttccgaaaat cggacttctt caagaacgcg  1620
gtcgttttttg caaactcacg tgtagaagtt tcgcgagacg aggtaactaa actgacaat  1680
cgattgaagg ccgatttcta ccaggtggac gtcagtcact cggcttctag gttgcttagt  1740
```

```
ctttttcagc cccacgaagc agaagacgat ataacagaaa aggggggcagt ttatacaatt    1800 cggaaaaaaa ttaaagatat gcctctaaac gtagttcttg ggacaatcgc tcgttttgaa    1860
gagtttagat ttgatgtcct aaagcactac tttccccatc ttaagtccac ccgggacttc    1920
gccataaagg aagattatct tgggaatatt gaaataactt ttaagagtga ccatgagact    1980
ctgtctgctt ccgacctgat cacagggtta gataaggttc tgcaaatagt cgctgaccat    2040
atctctaaga ttaaggttac ttaccaaggc accaagcaat ttgacgcaaa acgactagca    2100
tccgttctga gagataagcg agtgcaaatt gcaactccag ttgaaggcgg aataggcacc    2160
agccaagcat tcgctagtga tcctaaaaga cgagtcaacc tggaagaagc agattggtac    2220
gtctacaatg ataactttgg aacaagcgaa gagaagtcct tcgttgagta cttctccact    2280
gttgtgaatg atctaaaaaa gaaattcgat gaagtatatc tcgtgagaaa cgagcggcta    2340
gcagagttag ctatatactc ctttgataca ggggaacgct tcgagccaga ttttttgctg    2400 ttttaggaa aaaggatgt tccgggtac gaacagcagc aaatctacgt ggagcccaag    2460
ggaaatcacc tgctcgcaac tgaccagtgg aaggaaaatt tcctcttgga catccagcag    2520
aacgcagttc cccataccgt gtacgttgat gacaatgact accgcatcat cgggctgccc    2580
ttctataatg aaaagcatca gttgatggaa tttcgtgaag cattttctag agcaacggat    2640
ttataa                                                               2646
```

<210> SEQ ID NO 16
<211> LENGTH: 881
<212> TYPE: PRT
<213> ORGANISM: Corynebacterium glutamicum ssp. Lactofermentum

<400> SEQUENCE: 16

```
Val Ser Ser Ser Ala Thr Asp Leu Asp Leu Phe Leu Phe Gln Glu Leu
1               5                   10                  15

Asp Leu Phe Leu Asp Arg Phe Gly Lys Arg Lys Glu Val Pro Thr His
                20                  25                  30

Ile Ser Arg Asn Leu Ala Pro Gln Ile Ser Leu Arg Glu Tyr Gln Lys
            35                  40                  45

His Ala Phe Thr Asn Thr Leu Glu Tyr Leu Glu Asn Glu Ser Phe Ser
        50                  55                  60

Lys Asn Arg Gln Thr His Leu Leu Tyr His Met Ala Thr Gly Ser Gly
65                  70                  75                  80

Lys Thr Val Met Met Ala Gly Leu Ile Leu His Tyr Phe Ser Leu Gly
                85                  90                  95

Tyr Arg Asn Phe Leu Phe Phe Val Asn Gln Thr Asn Ile Ile Glu Lys
            100                 105                 110

Thr Lys Ser Asn Phe Leu Lys Pro Asp Ser Ser Lys Tyr Leu Phe Ala
        115                 120                 125

Asp His Ile Glu Ile Asn Gly Ala Pro Val Arg Ile Asn Glu Val Glu
    130                 135                 140

Thr Phe Ser Ala Ser Asp Pro Asn Ala Val Asn Ile Cys Phe Thr Thr
145                 150                 155                 160

Thr His Lys Leu His Gly Asp Phe Phe Phe Ala Thr Glu Asn Ser Leu
                165                 170                 175

Ser Gln Asp Asp Phe Glu Glu Ala Pro Val Val Met Ile Ser Asp Glu
            180                 185                 190

Ser His His Val Asn Thr Arg Thr Lys Lys Ala Thr Lys Ser Glu Lys
        195                 200                 205
```

```
Asp Glu Asp Ser Ser Trp Glu Tyr Thr Val Ser Ser Ala Phe Ala Ser
    210                 215                 220

Asn Arg Asp Asn Val Leu Leu Glu Phe Thr Ala Thr Val Asp Leu Arg
225                 230                 235                 240

Asp Arg Asn Ile Leu Ala Lys Tyr Arg Asn Lys Ile Val Phe Asp Tyr
                245                 250                 255

Pro Leu Ala Lys Phe Arg Asp Ser Gly Phe Thr Lys Asp Phe Gln Asn
            260                 265                 270

Phe Gln Ser Ser Leu Asp Pro Trp Gly Arg Thr Leu Gln Ala Leu Ile
        275                 280                 285

Leu Ser Glu Tyr Arg Arg Ser Leu Phe Ala Asp Gly Gly Val Tyr Ala
    290                 295                 300

Lys Pro Val Val Leu Lys Ser Gln Ala Ile Lys Glu Ser Asn Glu
305                 310                 315                 320

Phe Tyr Thr Glu Phe Phe Gln Arg Leu Arg Gln Leu Ser Glu Asp Arg
                325                 330                 335

Ile Arg Ser Phe Ala Thr Glu Glu Val Ile Gly Gln Ala Val Glu Tyr
            340                 345                 350

Phe Ala Ala Lys Asp Pro Thr Leu Arg Ser Leu Arg Ile Ser Leu Gln
        355                 360                 365

Gln Ser Phe Ala Glu Glu Asn Ala Ile Ile Met Asn Gly Ser Thr Asp
    370                 375                 380

Asn Thr Val Glu Lys Gln Leu Ala Val Asn Ser Leu Glu Asp His Ser
385                 390                 395                 400

Asn Pro Tyr Arg Ile Ile Phe Thr Val Asp Met Leu Asn Glu Gly Trp
                405                 410                 415

Asp Val Leu Asn Leu Tyr Asp Ile Val Arg Leu Tyr Glu Thr Arg Gln
            420                 425                 430

Gly Gly Lys Gly Gly Lys Pro Gly Ser Tyr Thr Ile Gln Glu Ala Gln
        435                 440                 445

Leu Ile Gly Arg Gly Ala Arg Tyr Phe Pro Phe Ile Leu Asn Lys Glu
    450                 455                 460

Leu Asp Ile Arg Glu Pro Glu Glu Ala Arg Val Arg Lys Tyr Asp Ala
465                 470                 475                 480

Asp Leu Glu Asn Pro His Arg Leu Leu Glu Thr Leu Leu Tyr His Ser
                485                 490                 495

Lys Gln Asp Ser Lys Tyr Ile Ala Glu Leu Arg Leu Ala Leu Arg Glu
            500                 505                 510

Thr Gly Leu Leu Pro Asn Asp Ile Thr Glu Val Thr Tyr Glu Val Lys
        515                 520                 525

Pro Asp Phe Arg Lys Ser Asp Phe Lys Asn Ala Val Val Phe Ala
    530                 535                 540

Asn Ser Arg Val Glu Val Ser Arg Asp Glu Val Thr Lys Leu Asp Asn
545                 550                 555                 560

Arg Leu Lys Ala Asp Phe Tyr Gln Val Asp Val Ser His Ser Ala Ser
                565                 570                 575

Arg Leu Leu Ser Leu Phe Gln Pro His Glu Ala Glu Asp Asp Ile Thr
            580                 585                 590

Glu Lys Gly Ala Val Tyr Thr Ile Arg Lys Lys Ile Lys Asp Met Pro
        595                 600                 605

Leu Asn Val Val Leu Gly Thr Ile Ala Arg Phe Glu Glu Phe Arg Phe
    610                 615                 620
```

-continued

```
Asp Val Leu Lys His Tyr Phe Pro His Leu Lys Ser Thr Arg Asp Phe
625                 630                 635                 640

Ala Ile Lys Glu Asp Tyr Leu Gly Asn Ile Glu Ile Thr Phe Lys Ser
            645                 650                 655

Asp His Glu Thr Leu Ser Ala Ser Asp Leu Ile Thr Gly Leu Asp Lys
        660                 665                 670

Val Leu Gln Ile Val Ala Asp His Ile Ser Lys Ile Lys Val Thr Tyr
    675                 680                 685

Gln Gly Thr Lys Gln Phe Asp Ala Lys Arg Leu Ala Ser Val Leu Arg
690                 695                 700

Asp Lys Arg Val Gln Ile Ala Thr Pro Val Glu Gly Ile Gly Thr
705                 710                 715                 720

Ser Gln Ala Phe Ala Ser Asp Pro Lys Arg Arg Val Asn Leu Glu Glu
            725                 730                 735

Ala Asp Trp Tyr Val Tyr Asn Asp Asn Phe Gly Thr Ser Glu Glu Lys
        740                 745                 750

Ser Phe Val Glu Tyr Phe Ser Thr Val Asn Asp Leu Lys Lys Lys
    755                 760                 765

Phe Asp Glu Val Tyr Leu Val Arg Asn Glu Arg Leu Ala Glu Leu Ala
770                 775                 780

Ile Tyr Ser Phe Asp Thr Gly Glu Arg Phe Glu Pro Asp Phe Leu Leu
785                 790                 795                 800

Phe Leu Gly Lys Lys Asp Val Ser Gly Tyr Glu Gln Gln Gln Ile Tyr
            805                 810                 815

Val Glu Pro Lys Gly Asn His Leu Leu Ala Thr Asp Gln Trp Lys Glu
        820                 825                 830

Asn Phe Leu Leu Asp Ile Gln Gln Asn Ala Val Pro His Thr Val Tyr
    835                 840                 845

Val Asp Asp Asn Asp Tyr Arg Ile Ile Gly Leu Pro Phe Tyr Asn Glu
850                 855                 860

Lys His Gln Leu Met Glu Phe Arg Glu Ala Phe Ser Arg Ala Thr Asp
865                 870                 875                 880

Leu
```

<210> SEQ ID NO 17
<211> LENGTH: 1608
<212> TYPE: DNA
<213> ORGANISM: Corynebacterium glutamicum ssp. Lactofermentum

<400> SEQUENCE: 17

```
atgagcaagg tattcggtat cgatctcggc accacctatt cagccatcgc acatatcacc    60
gattctgaca cggtcgaaat cattgacaat gctgacggtc agagcaccac tccgtccgtc   120
gtatttttg aagatgcaac aaacgtcgtg gtgggagcaa ctgctaagca gggtgcgaag   180
ttcaaccctg agcagaccgt gtctctgatc aaacgcgaaa tgggtcggaa gggtcccgag   240
gtggaacgcc agttcttcgg caacacatat accccggaat ccatctctgc gatcatcctg   300
cgtgagttga tcgaaaatgc aatggaggag gtggatacag actcgaaaaa ggcagtaatc   360
actgtcccgg cctacttcgg actgaatgaa agaattcca ccaaactcgc gggtgagatt   420
gcgggtattg acgtgatcga tattgtttcc gaacctgtgg cagctgcgat gctgaggga   480
tttgatttca cacgggaaga aactgtcctt gtctatgacc tgggtggtgg caccttcgac   540
tgcaccatca tgaccttcag ccctgatgag ggtatccagg tgaaggctgt tgatggtgac   600
agaacattgg gaggcgctga ttgggataag gcgctctatg atttcgtcct cgatcagttc   660
```

```
cgggaggcat gcgcctctca gttgggagat gagtaccccg aagatgatgt cgcctttgtt      720
caggaactcc agaacgccgc tgagaacgcc aagatcagcc tgaccaagaa gacgaaggtc      780
cgcgtcccct gtgcttatgc aggcgcctcc acgctcgtcg aggtcactca ggaggatttc      840
gagcgtgcga ctcgccatct tctcgaccga accctggagt gcgttgatcg cactcttggt      900
ctggggaaca agaatttccc tggcctcaag gtggataagt acctcctggt cggtggctct      960
tcccgcatgc ctcaggtggc tgacgcgctc accgagaaat acggttggac acttcaaaag     1020
acgcactttg accacgcggt tgccaaggga gcagccatga ttgggcaggg aatcgtggag     1080
gtaccccgctg agacaacgg cctgcccgat aagcaggagg ggcccaggga gctgctgctt     1140
cccggccatg ccaggctgg aaccatgacc attcagaatc tactgtccaa ggccgtgggc     1200
gttaagttca gtaacgagga tggctcccaa tacatcggac acctcatcga gcagaacacc     1260
ccactgcccg cagagggctc tgtgaaggcg tccacccctcg cgatagtgt gcagagtctt     1320
cccgttcacc ttttcgaaca aaagggtgag gtccccagtg aagaactcgg cgcgaatgtg     1380
gagatcaccc cggaaagtgg cgccatttc actgaccttc ccaacctgcc caagggtca      1440
cccatccaca tgaccatgaa agtcgacgct tcaggccttc ttcatttcga gggttatgaa     1500
ccgtcgaccg accagtacct gcgtttggag attgaggtgt ccaccatgca gcgggaagaa     1560
gtggagagag cgaaagaagt tgtctcgagc ctgacccgga atgagtag                  1608
```

<210> SEQ ID NO 18
<211> LENGTH: 535
<212> TYPE: PRT
<213> ORGANISM: Corynebacterium glutamicum ssp. Lactofermentum

<400> SEQUENCE: 18

Met Ser Lys Val Phe Gly Ile Asp Leu Gly Thr Thr Tyr Ser Ala Ile
1               5                   10                  15

Ala His Ile Thr Asp Ser Asp Thr Val Glu Ile Ile Asp Asn Ala Asp
            20                  25                  30

Gly Gln Ser Thr Thr Pro Ser Val Val Phe Glu Asp Ala Thr Asn
        35                  40                  45

Val Val Val Gly Ala Thr Ala Lys Gln Gly Ala Lys Phe Asn Pro Glu
    50                  55                  60

Gln Thr Val Ser Leu Ile Lys Arg Glu Met Gly Arg Lys Gly Pro Glu
65                  70                  75                  80

Val Glu Arg Gln Phe Phe Gly Asn Thr Tyr Thr Pro Glu Ser Ile Ser
                85                  90                  95

Ala Ile Ile Leu Arg Glu Leu Ile Glu Asn Ala Met Glu Glu Val Asp
            100                 105                 110

Thr Asp Ser Lys Lys Ala Val Ile Thr Val Pro Ala Tyr Phe Gly Leu
        115                 120                 125

Asn Glu Lys Asn Ser Thr Lys Leu Ala Gly Glu Ile Ala Gly Ile Asp
    130                 135                 140

Val Ile Asp Ile Val Ser Glu Pro Val Ala Ala Ile Ala Glu Gly
145                 150                 155                 160

Phe Asp Phe Thr Arg Glu Glu Thr Val Leu Val Tyr Asp Leu Gly Gly
                165                 170                 175

Gly Thr Phe Asp Cys Thr Ile Met Thr Phe Ser Pro Asp Glu Gly Ile
            180                 185                 190

Gln Val Lys Ala Val Asp Gly Asp Arg Thr Leu Gly Gly Ala Asp Trp
        195                 200                 205

```
Asp Lys Ala Leu Tyr Asp Phe Val Leu Asp Gln Phe Arg Glu Ala Cys
    210                 215                 220

Ala Ser Gln Leu Gly Asp Glu Tyr Pro Glu Asp Val Ala Phe Val
225                 230                 235                 240

Gln Glu Leu Gln Asn Ala Ala Glu Asn Ala Lys Ile Ser Leu Thr Lys
            245                 250                 255

Lys Thr Lys Val Arg Val Pro Cys Ala Tyr Ala Gly Ala Ser Thr Leu
            260                 265                 270

Val Glu Val Thr Gln Glu Asp Phe Glu Arg Ala Thr Arg His Leu Leu
            275                 280                 285

Asp Arg Thr Leu Glu Cys Val Asp Arg Thr Leu Gly Leu Gly Asn Lys
            290                 295                 300

Asn Phe Pro Gly Leu Lys Val Asp Lys Tyr Leu Leu Val Gly Gly Ser
305                 310                 315                 320

Ser Arg Met Pro Gln Val Ala Asp Ala Leu Thr Glu Lys Tyr Gly Trp
                325                 330                 335

Thr Leu Gln Lys Thr His Phe Asp His Ala Val Ala Lys Gly Ala Ala
            340                 345                 350

Met Ile Gly Gln Gly Ile Val Glu Val Pro Ala Gly Asp Asn Gly Leu
            355                 360                 365

Pro Asp Lys Gln Glu Gly Pro Arg Glu Leu Leu Leu Pro Gly His Gly
370                 375                 380

Gln Ala Gly Thr Met Thr Ile Gln Asn Leu Leu Ser Lys Ala Val Gly
385                 390                 395                 400

Val Lys Phe Ser Asn Glu Asp Gly Ser Gln Tyr Ile Gly His Leu Ile
                405                 410                 415

Glu Gln Asn Thr Pro Leu Pro Ala Glu Gly Ser Val Lys Ala Ser Thr
            420                 425                 430

Leu Gly Asp Ser Val Gln Ser Leu Pro Val His Leu Phe Glu Gln Lys
            435                 440                 445

Gly Glu Val Pro Ser Glu Glu Leu Gly Ala Asn Val Glu Ile Thr Pro
450                 455                 460

Glu Ser Gly Ala Ile Phe Thr Asp Leu Pro Asn Leu Pro Lys Gly Ser
465                 470                 475                 480

Pro Ile His Met Thr Met Lys Val Asp Ala Ser Gly Leu Leu His Phe
                485                 490                 495

Glu Gly Tyr Glu Pro Ser Thr Asp Gln Tyr Leu Arg Leu Glu Ile Glu
            500                 505                 510

Val Ser Thr Met Gln Arg Glu Glu Val Glu Arg Ala Lys Glu Val Val
            515                 520                 525

Ser Ser Leu Thr Arg Asn Glu
    530                 535

<210> SEQ ID NO 19
<211> LENGTH: 1125
<212> TYPE: DNA
<213> ORGANISM: Corynebacterium glutamicum ssp. Lactofermentum

<400> SEQUENCE: 19
atgttcgagc taatcgacga ctggggtccc gaaaagatcg tcatcgtcag cgatcaaaaa      60
accgggatgc gtggcgtact tgtcatcgac aacaccgccc gcggcatggg caagggcggc     120
acgcgcatgc agcccaccgt ttcagtcgca gaaatagcca ggttggctcg cgtcatgacc     180
tggaaatggg ctggtgtaga cctcttttat ggtggtgcaa aagccggaat ccaagcagac     240
```

-continued

```
cccacctccc cagataaaga agcaatcctt cggtcattcg tcagaaaact ctccaacgaa      300
gtacctaaag aatatgtctt cggcctggac atggggctga ctgaaaatga cgccgccatc      360
atcgtcgacg agctcggctg gggcaccagt atgggaacac cctacgagct cggtggagtg      420
ccctacgaca agcttggtat caccggcttt ggtgttgcag aagtggtgga tcaagtagca      480
caaatgcaaa aactcaaagg tgcatcggta gcagtccaag gcttcggtgc cgttggacat      540
gccacagctt cccgcctggc agaacttggc tatcctgttg tggctatctc cacagcaaag      600
ggagcaatcg cagaccccaa cgggctcaac atccccgagc tcatggaact acgcgatcag      660
gtgggtgact cacttgtgga ccactaccca gcacttcgca tcaacccagg tgacgaactt      720
ttcaccgaag ccgaaatcct cgtaccggca gcgctccagg acgtcatcga tgaagacgca      780
gccaatcgac tacaagcaca actcgtcgtc gaaggagcaa accttcccac taatgaagcc      840
gcacaaaaag tcctaagtaa ccgtggcatc actgtggttc cagactttgt cgccaacgcc      900
ggaggagtag tcgccgcagc attcgccatg gataaccgca tgtctgcatt ccgtgcagag      960
actgccaaca tcttcacgag cgtttccgac aaactccgat ccaatgccga aactgtcctg     1020
aatttcacct ctgaatctga cctgaccagc cacgaagcgg caaggcaact ttcacaggaa     1080
cgagttcttg cagctatgcg cgccagaggt atggttcgcc gataa                    1125
```

<210> SEQ ID NO 20
<211> LENGTH: 374
<212> TYPE: PRT
<213> ORGANISM: Corynebacterium glutamicum ssp. Lactofermentum

<400> SEQUENCE: 20

```
Met Phe Glu Leu Ile Asp Asp Trp Gly Pro Glu Lys Ile Val Ile Val
 1               5                  10                  15

Ser Asp Gln Lys Thr Gly Met Arg Gly Val Leu Val Ile Asp Asn Thr
            20                  25                  30

Ala Arg Gly Met Gly Lys Gly Gly Thr Arg Met Gln Pro Thr Val Ser
        35                  40                  45

Val Ala Glu Ile Ala Arg Leu Ala Arg Val Met Thr Trp Lys Trp Ala
    50                  55                  60

Gly Val Asp Leu Phe Tyr Gly Gly Ala Lys Ala Gly Ile Gln Ala Asp
65                  70                  75                  80

Pro Thr Ser Pro Asp Lys Glu Ala Ile Leu Arg Ser Phe Val Arg Lys
                85                  90                  95

Leu Ser Asn Glu Val Pro Lys Glu Tyr Val Phe Gly Leu Asp Met Gly
            100                 105                 110

Leu Thr Glu Asn Asp Ala Ala Ile Ile Val Asp Glu Leu Gly Trp Gly
        115                 120                 125

Thr Ser Met Gly Thr Pro Tyr Glu Leu Gly Gly Val Pro Tyr Asp Lys
    130                 135                 140

Leu Gly Ile Thr Gly Phe Gly Val Ala Glu Val Val Asp Gln Val Ala
145                 150                 155                 160

Gln Met Gln Lys Leu Lys Gly Ala Ser Val Ala Val Gln Gly Phe Gly
                165                 170                 175

Ala Val Gly His Ala Thr Ala Ser Arg Leu Ala Glu Leu Gly Tyr Pro
            180                 185                 190

Val Val Ala Ile Ser Thr Ala Lys Gly Ala Ile Ala Asp Pro Asn Gly
        195                 200                 205

Leu Asn Ile Pro Glu Leu Met Glu Leu Arg Asp Gln Val Gly Asp Ser
```

-continued

```
                210                 215                 220
Leu Val Asp His Tyr Pro Ala Leu Arg Ile Asn Pro Gly Asp Glu Leu
225                 230                 235                 240
Phe Thr Glu Ala Glu Ile Leu Val Pro Ala Ala Leu Gln Asp Val Ile
                245                 250                 255
Asp Glu Asp Ala Ala Asn Arg Leu Gln Ala Gln Leu Val Val Glu Gly
                260                 265                 270
Ala Asn Leu Pro Thr Asn Glu Ala Ala Gln Lys Val Leu Ser Asn Arg
            275                 280                 285
Gly Ile Thr Val Val Pro Asp Phe Val Ala Asn Ala Gly Gly Val Val
        290                 295                 300
Ala Ala Ala Phe Ala Met Asp Asn Arg Met Ser Ala Phe Arg Ala Glu
305                 310                 315                 320
Thr Ala Asn Ile Phe Thr Ser Val Ser Asp Lys Leu Arg Ser Asn Ala
                325                 330                 335
Glu Thr Val Leu Asn Phe Thr Ser Glu Ser Asp Leu Thr Ser His Glu
                340                 345                 350
Ala Ala Arg Gln Leu Ser Gln Glu Arg Val Leu Ala Ala Met Arg Ala
            355                 360                 365
Arg Gly Met Val Arg Arg
        370

<210> SEQ ID NO 21
<211> LENGTH: 1314
<212> TYPE: DNA
<213> ORGANISM: Corynebacterium glutamicum ssp. Lactofermentum

<400> SEQUENCE: 21
atgtctgttc aaaacccggc aatagtaagt gccacgccag acaccacaat tagcaacaca        60
atcagcacct ctgaaatcag caaaaaagac cttaagaatg cagtacgtgc aagcttcatt      120
ggaacttttg ttgaatggtt cgactacgcc gcatatatgt acatggcatc catcatcgcg      180
ggagttttct cccggagct caccggacgt gcagcacttg ttaacacttt cgccctattt       240
gcactctcat tcctcattcg tcctatcggc gcagttgcct ggggacacat cggagaccgc      300
cttggccgca ccaagagcct ttccgcgtca atcctcttta tgagccttgc cactttctgt      360
attgcattac ttcccgggta caactccatc ggtattgtcg caccaatctt gcttttggta      420
ctacgcctta tccagggatt tagtgcttcc ggcgaatatg ccgcagcagc tacctatatc      480
tcagaatctg ccccacagaa ccgtcgtgga cttttcgcct cagtagttcc cgcagcgacc      540
gcttgtggac tcctccttgg ttctctcttc gccgctcttc tcacttccct ccttgacgat      600
gcttccctcg cttcctgggg ttggcgccta ccattccttt ggcagcacc tctaggaatt       660 gttggcctca tcatccgccg catggccccc gaaactcacg tagcagacga agactccgct      720
aaaaagcttc caatcctcga ggttttcaaa tacccacgtg cacttcttgt agctttctcc      780
ggcgccatcc tcaatgccat cggtttctac atagttctgg cctacctacc tacttatctt      840
tccgaagaac tcggcatgag ctctagcagt gctttatcg ctaccaccat ctcctccgca       900
gtttatgcag tcctcgtcgt cgcaaccggc gcactctctg accacctagg ccgccgcacc      960
acaatgctta tggccgcagc acttttttgca gtattttcaa ttcctgcttt cctcgcgcta    1020
gacagcgcaa gcttcgccgg aatcattttg atccaggtcg aatgggtgc cttccttgcg      1080 cttaacgacg gagtgctccc gtccttcatc tccgaacaat tcccacctga tgttcgactc     1140
accggctttg cccttacttt caactgcgcg aatgccttct ttggcggcac cgcagcgatg    1200
```

```
atcgcaacct ggatgatcgg tgccagtggc aacgtaattg caccggccta ctacatggtc    1260
gcagctgcaa tcattaccgc aattggtgtc acattcgccg caaagtccaa atag          1314
```

<210> SEQ ID NO 22
<211> LENGTH: 437
<212> TYPE: PRT
<213> ORGANISM: Corynebacterium glutamicum ssp. Lactofermentum

<400> SEQUENCE: 22

```
Met Ser Val Gln Asn Pro Ala Ile Val Ser Ala Thr Pro Asp Thr Thr
1               5                   10                  15

Ile Ser Asn Thr Ile Ser Thr Glu Ile Ser Lys Lys Asp Leu Lys
            20                  25                  30

Asn Ala Val Arg Ala Ser Phe Ile Gly Thr Phe Val Glu Trp Phe Asp
        35                  40                  45

Tyr Ala Ala Tyr Met Tyr Met Ala Ser Ile Ile Ala Gly Val Phe Phe
    50                  55                  60

Pro Glu Leu Thr Gly Arg Ala Ala Leu Val Asn Thr Phe Ala Leu Phe
65                  70                  75                  80

Ala Leu Ser Phe Leu Ile Arg Pro Ile Gly Ala Val Ala Trp Gly His
                85                  90                  95

Ile Gly Asp Arg Leu Gly Arg Thr Lys Ser Leu Ser Ala Ser Ile Leu
            100                 105                 110

Phe Met Ser Leu Ala Thr Phe Cys Ile Ala Leu Leu Pro Gly Tyr Asn
        115                 120                 125

Ser Ile Gly Ile Val Ala Pro Ile Leu Leu Leu Val Leu Arg Leu Ile
    130                 135                 140

Gln Gly Phe Ser Ala Ser Gly Glu Tyr Ala Ala Ala Thr Tyr Ile
145                 150                 155                 160

Ser Glu Ser Ala Pro Gln Asn Arg Arg Gly Leu Phe Ala Ser Val Val
                165                 170                 175

Pro Ala Ala Thr Ala Cys Gly Leu Leu Leu Gly Ser Leu Phe Ala Ala
            180                 185                 190

Leu Leu Thr Ser Leu Leu Asp Asp Ala Ser Leu Ala Ser Trp Gly Trp
        195                 200                 205

Arg Leu Pro Phe Leu Leu Ala Ala Pro Leu Gly Ile Val Gly Leu Ile
    210                 215                 220

Ile Arg Arg Met Ala Pro Glu Thr His Val Ala Asp Glu Asp Ser Ala
225                 230                 235                 240

Lys Lys Leu Pro Ile Leu Glu Val Phe Lys Tyr Pro Arg Ala Leu Leu
                245                 250                 255

Val Ala Phe Ser Gly Ala Ile Leu Asn Ala Ile Gly Phe Tyr Ile Val
            260                 265                 270

Leu Ala Tyr Leu Pro Thr Tyr Leu Ser Glu Glu Leu Gly Met Ser Ser
        275                 280                 285

Ser Ser Ala Phe Ile Ala Thr Thr Ile Ser Ser Ala Val Tyr Ala Val
    290                 295                 300

Leu Val Val Ala Thr Gly Ala Leu Ser Asp His Leu Gly Arg Arg Thr
305                 310                 315                 320

Thr Met Leu Met Ala Ala Ala Leu Phe Ala Val Phe Ser Ile Pro Ala
                325                 330                 335

Phe Leu Ala Leu Asp Ser Ala Ser Phe Ala Gly Ile Ile Leu Ile Gln
            340                 345                 350
```

-continued

```
Val Gly Met Gly Ala Phe Leu Ala Leu Asn Asp Gly Val Leu Pro Ser
        355                 360                 365

Phe Ile Ser Glu Gln Phe Pro Pro Asp Val Arg Leu Thr Gly Phe Ala
        370                 375                 380

Leu Thr Phe Asn Cys Ala Asn Ala Phe Phe Gly Gly Thr Ala Ala Met
385                 390                 395                 400

Ile Ala Thr Trp Met Ile Gly Ala Ser Gly Asn Val Ile Ala Pro Ala
                405                 410                 415

Tyr Tyr Met Val Ala Ala Ala Ile Ile Thr Ala Ile Gly Val Thr Phe
            420                 425                 430

Ala Ala Lys Ser Lys
            435
```